(12) United States Patent
Yang

(10) Patent No.: US 10,532,084 B2
(45) Date of Patent: *Jan. 14, 2020

(54) CHONDROCYTE EXTRACELLULAR MATRIX-DERIVED PEPTIDE

(71) Applicant: EYEBIO KOREA, Gimhae-si, Gyeongsangnam-do (KR)

(72) Inventor: Jae Wook Yang, Busan (KR)

(73) Assignee: EYEBIO KOREA, Gimhae-si, Gyeongsangnam-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/178,618

(22) Filed: Nov. 2, 2018

(65) Prior Publication Data

US 2019/0100572 A1 Apr. 4, 2019

Related U.S. Application Data

(63) Continuation of application No. 16/091,998, filed as application No. PCT/KR2017/001419 on Feb. 9, 2017.

(30) Foreign Application Priority Data

| Apr. 8, 2016 | (KR) | 10-2016-0043296 |
| Apr. 8, 2016 | (KR) | 10-2016-0043298 |
| Apr. 8, 2016 | (KR) | 10-2016-0043300 |
| Apr. 8, 2016 | (KR) | 10-2016-0043305 |

(51) Int. Cl.

| C07K 14/78 | (2006.01) |
| A61K 38/39 | (2006.01) |
| A61K 38/08 | (2019.01) |
| A61K 9/00 | (2006.01) |
| A61K 9/08 | (2006.01) |
| C07K 7/06 | (2006.01) |
| A23L 33/18 | (2016.01) |
| A61P 27/02 | (2006.01) |
| A61K 38/00 | (2006.01) |

(52) U.S. Cl.
CPC .............. *A61K 38/39* (2013.01); *A23L 33/18* (2016.08); *A61K 9/00* (2013.01); *A61K 9/0048* (2013.01); *A61K 9/08* (2013.01); *A61K 38/08* (2013.01); *A61P 27/02* (2018.01); *C07K 7/06* (2013.01); *C07K 14/78* (2013.01); *A61K 38/00* (2013.01)

(58) Field of Classification Search
CPC ........ A61K 9/0019; C07K 14/47; A61P 27/02
See application file for complete search history.

(56) References Cited

U.S. PATENT DOCUMENTS

| 6,110,689 A | 8/2000 | Qvist et al. |
| 7,718,366 B2 | 5/2010 | Tsai et al. |
| 2005/0096257 A1 | 5/2005 | Shima et al. |
| 2009/0131303 A1 | 5/2009 | Hong et al. |
| 2014/0037712 A1 | 2/2014 | Yoon et al. |
| 2016/0215018 A1 | 7/2016 | Yang et al. |

FOREIGN PATENT DOCUMENTS

| DE | 4041059 A1 * | 6/1992 | ............. C07K 14/78 |
| KR | 10-2006-0121836 A | 11/2006 | |
| KR | 10-2010-0087188 A | 8/2010 | |
| KR | 10-1438744 B1 | 9/2014 | |
| KR | 10-2016-0079983 A | 7/2016 | |
| WO | WO2007102736 A2 * | 9/2007 | ............... C12Q 1/68 |

OTHER PUBLICATIONS

Wang et al. The role of anti-inflammatory agents in age-related macular degeneration (AMD) treatment. Eye 2011; 25:127-139. (Year: 2011).*
Top foods to help protect your vision. Harvard Health Letter. Aug. 2013. https://www.health.harvard.edu/staying-healthy/top-foods-to-help-protect-your-vision[Mar. 14, 2019 11:09:01 PM] (Year: 2013).*
International Search Report for PCT/KR2017/001419 dated May 24, 2017 from Korean Intellectual Property Office.

* cited by examiner

*Primary Examiner* — Marcela M Cordero Garcia
*Assistant Examiner* — Jia-Hai Lee
(74) *Attorney, Agent, or Firm* — Revolution IP, PLLC

(57) ABSTRACT

Disclosed is a novel peptide capable of preventing or treating ocular surface disease by inhibiting or improving pathological changes caused by neovascularization, opacification, fibrosis and inflammation of the cornea, the peptide having an amino acid sequence represented by SEQ ID NO: 1 and more particularly, provides a collagen type II α1-based peptide isolated from an animal chondrocyte cell-derived extracellular matrix and use thereof.

6 Claims, 17 Drawing Sheets

Specification includes a Sequence Listing.

FIG. 1

Certificate of Analysis
BIOCELTRAN

RM# 304, BIO2. Bldg., 32, Soyanggang-ro, Chuncheon-si, Gangwon-Do, South Korea
TEL: 033-258-6780 FAX: 033-258-6781 E-MAIL: sales@bioceltran.com

| Product Name | Collagen Type II α Peptide | | |
|---|---|---|---|
| Molecular Weight | 954.99 | | |
| Batch No. | CT160104 | Quantity | 3g |
| Sequence | Hyp GQ DG LAGPK (Hyp=Hydroxy proline) | | |
| TEST | SPECIFICATION | RESULT | |
| Appearance | White Powder | White Powder | |
| IDENTIFICATION — A. Identification By HPLC | Retention time is same with the reference substance | Conforms | |
| IDENTIFICATION — B. Molecular Ion Mass | 954.99 ± 1 | Conforms | |
| Purity (HPLC) | NLT 99% | 99.5% | |
| Related Substances (HPLC) | Total impurities: NMT1.0% / Single impurities: NMT1.0% | Total impurities: 0.5% / Single impurities: 0.46% | |
| Storage | Preserve in tight containers. Store at a temperature 2 to 8°C. | | |
| Conclusion : This batch of product complies with in-house standard. | | | |

Remark : This peptide was prepared by chemical synthesis.

Quality Control Date: JAN. 04, 2016

Quality Assurance by: Ji An Kim 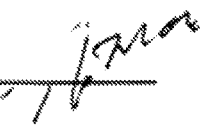

FIG. 9
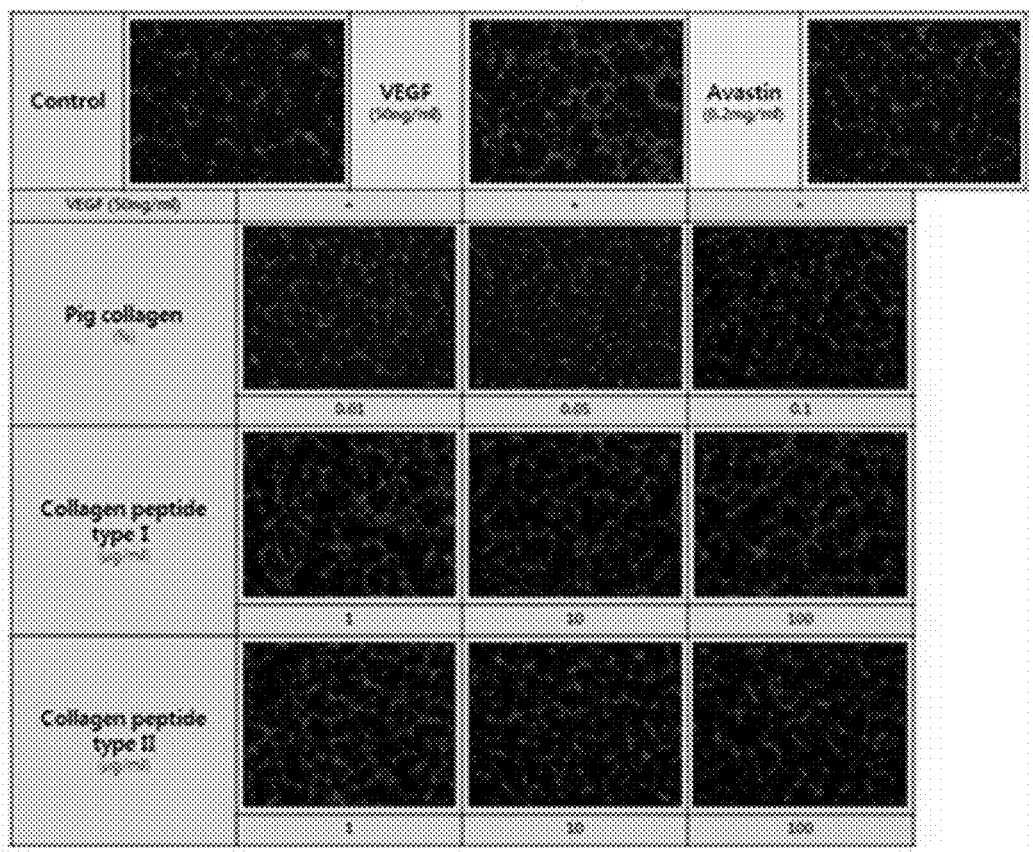
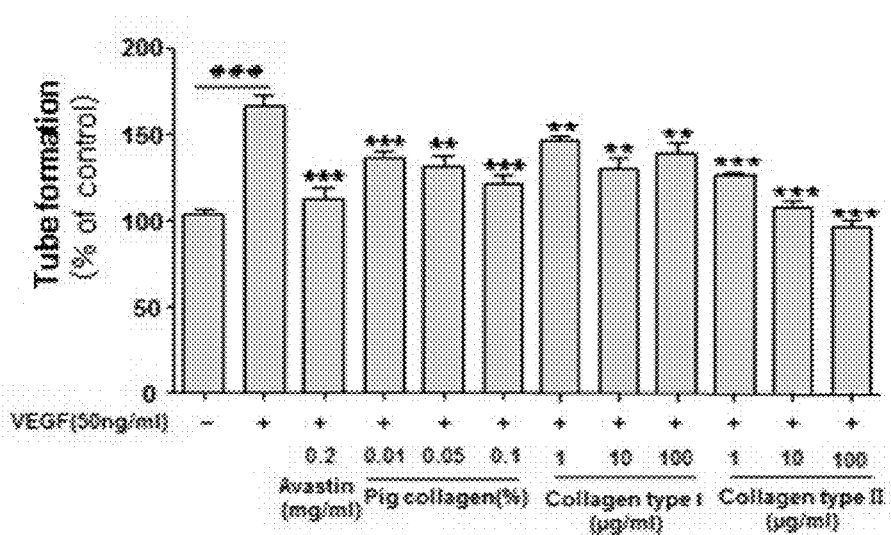

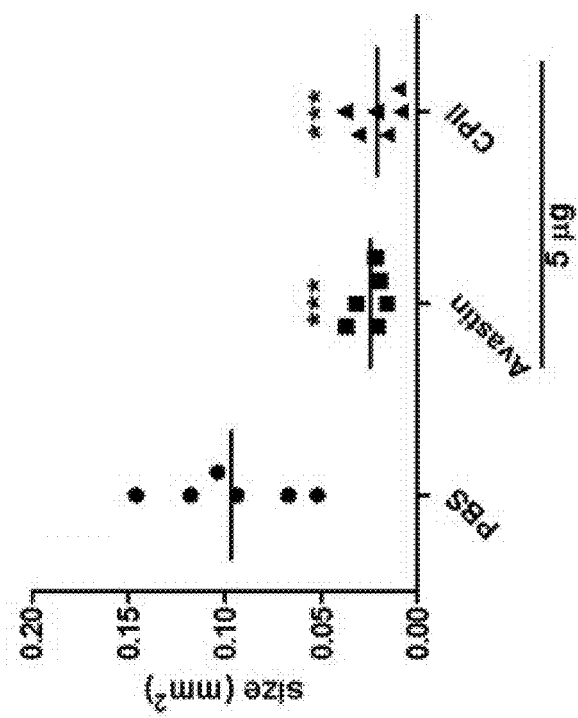
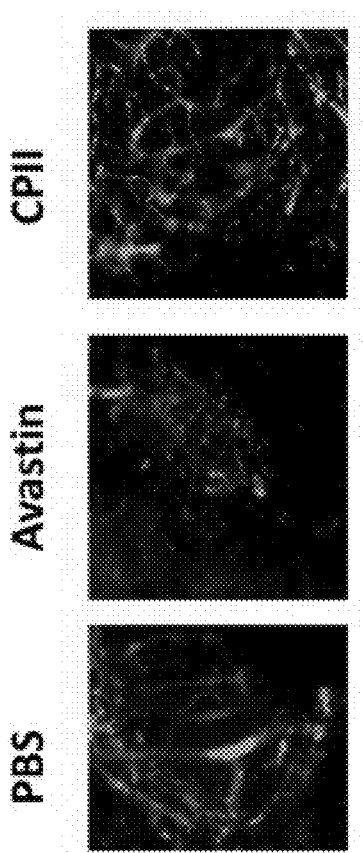
FIG. 12

SEQUENCE LISTING

```
<160> NUMBER OF SEQ ID NOS: 9

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is Hydroxy proline

<400> SEQUENCE: 1

Xaa Gly Gln Asp Gly Leu Ala Gly Pro Lys
1               5                   10

<210> SEQ ID NO 2
<211> LENGTH: 24
<212> TYPE: DNA
<213> ORGANISM: Artificial Sequence
<220> FEATURE:
<223> OTHER INFORMATION: VEGF forward primer

<400> SEQUENCE: 2
atgaactttc tgctgtcttg ggtg                                            24

<210> SEQ ID NO 3
<211> LENGTH: 21
<212> TYPE: DNA
<213> ORGANISM: Artificial Sequence
<220> FEATURE:
<223> OTHER INFORMATION: VEGF backward primer

<400> SEQUENCE: 3
tcaccgcctc ggcttgtcac a                                               21

<210> SEQ ID NO 4
<211> LENGTH: 23
<212> TYPE: DNA
<213> ORGANISM: Artificial Sequence
<220> FEATURE:
<223> OTHER INFORMATION: ICAM forward primer

<400> SEQUENCE: 4
tgcgttttgg agctagcgga cca                                             23

<210> SEQ ID NO 5
<211> LENGTH: 24
<212> TYPE: DNA
<213> ORGANISM: Artificial Sequence
<220> FEATURE:
<223> OTHER INFORMATION: ICAM backward primer

<400> SEQUENCE: 5
cgaggaccat acagcacgtg ccag                                            24

<210> SEQ ID NO 6
<211> LENGTH: 20
<212> TYPE: DNA
<213> ORGANISM: Artificial Sequence
<220> FEATURE:
<223> OTHER INFORMATION: MCP-1 forward primer

<400> SEQUENCE: 6
tggcaagatg atcccaatga                                                 20
```

```
<210> SEQ ID NO 7
<211> LENGTH: 21
<212> TYPE: DNA
<213> ORGANISM: Artificial Sequence
<220> FEATURE:
<223> OTHER INFORMATION: MCP-1 backward primer

<400> SEQUENCE: 7
gcagcactgt tcgtcacttc a                                              21

<210> SEQ ID NO 8
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 8
atggtgaagg tcggtgtgaa c                                              21

<210> SEQ ID NO 9
<211> LENGTH: 21
<212> TYPE: DNA
<213> ORGANISM: Artificial Sequence
<220> FEATURE:
<223> OTHER INFORMATION: GAPDH backward primer

<400> SEQUENCE: 9
gtgccgttga atttgccgtg a                                              21
```

US 10,532,084 B2

CHONDROCYTE EXTRACELLULAR MATRIX-DERIVED PEPTIDE

CROSS REFERENCE TO PRIOR APPLICATION

This application is a Continuation Application of U.S. patent application Ser. No. 16/091,998 filed on Oct. 8, 2018 under 35 U.S.C. § 120, which is the 35 U.S.C. 371 national stage of International application PCT/KR2017/001419 filed on Feb. 9, 2017; which claims priority to Korean applications 10-2016-0043300 filed on Apr. 8, 2016, 10-2016-0043305 filed on Apr. 8, 2016, 10-2016-0043298 filed on Apr. 8, 2016, and 10-2016-0043296 filed on Apr. 8, 2016. The entire contents of each of the above-identified applications are hereby incorporated by reference.

BACKGROUND

The present invention relates to novel peptides and uses thereof. The extracellular matrix (ECM) is a remaining component in the tissue other than the cells is composed of three-dimensional combinations of various structural and functional molecules secreted by cells, and it cannot be manufactured artificially because the characteristics and functions thereof are not yet fully identified. The extracellular matrix plays an important role in maintaining the cellular environment while determining the physical properties of the tissue such as the distraction force, the compressive strength and the elasticity in the tissue shape and controlling the osmotic pressure, permeability of ions, etc.

In addition, it has a lot of growth factors and cytokines, and plays a role in determining the function of cells and in particular, it regulates differentiation of cells in the fetal and growing stages or suggests the direction of tissue growth while increasing or decreasing cell adhesion and metabolic activity.

The extracellular matrix has proteins such as collagen and elastin to determine the physical properties of the tissue and glycoproteins such as fibronectin and laminin to attach cells and extracellular matrix and many proteoglycans such as chondroitin sulfate serve as a support to keep the volume by maintaining the shape and volume of the tissue and actively interacting with the cells in the tissue so as to maintain and function as a unique tissue or organ, however the components and structure of extracellular matrix have not yet been completely clarified.

It is an object of the present invention to provide a novel peptide capable of preventing or treating ocular surface disease by inhibiting or improving pathological changes caused by neovascularization, opacification, fibrosis and inflammation of the cornea.

SUMMARY

The present invention provides a peptide having an amino acid sequence represented by SEQ ID NO: 1.

The present invention provides a pharmaceutical composition for preventing or treating an ocular surface disease comprising a peptide having an amino acid sequence represented by SEQ ID NO: 1, as an active ingredient.

The present invention provides a health food for preventing or improving an ocular surface disease comprising a peptide having an amino acid sequence represented by SEQ ID NO: 1, as an active ingredient.

The present invention provides a pharmaceutical composition for preventing or treating macular degeneration comprising a peptide having the amino acid sequence of SEQ ID NO: 1, as an active ingredient.

The present invention provides a health food for preventing or improving macular degeneration comprising a peptide having an amino acid sequence of SEQ ID NO: 1, as an active ingredient.

The present invention provides a pharmaceutical composition for preventing or treating dry eye comprising a peptide having an amino acid sequence represented by SEQ ID NO: 1, as an active ingredient.

The present invention provides a health food for preventing or improving dry eye comprising a peptide having an amino acid sequence represented by SEQ ID NO: 1, as an active ingredient.

The novel peptide of the present invention has been confirmed that it reduces corneal opacity, neovascularization and fibrosis and inhibits the expression of inflammation-induced factors in animal models in which pathological changes of the ocular surface are induced by alkaline burn, and prevents and improves macular degeneration by effectively inhibiting angiogenesis in retina and choroid in which the tissue change is induced and inhibits or improves the pathological changes of the corneal epithelial cell such as the decrease in tear volume of eyeball, irregularity of corneal surface and the loss of conjunctival goblet cells, and accordingly can provide compositions comprising the same as an active ingredient as a pharmaceutical composition and a health food for preventing or treating ocular diseases.

BRIEF DESCRIPTION OF THE DRAWINGS

FIG. 1 is a report of the synthesized hydroxy proline-GQDGLAGPK (SEQ ID NO: 1) peptide.

FIG. 4A is a photograph of a rabbit cornea by a microscope (SZX7, Olympus, Tokyo, Japan) on days 0, 7 and 17 after alkaline burn (Scale bar=10 mm); FIG. 4B is a graph showing the degree of corneal neovascularization; and FIG. 4C is a graph showing the degree of corneal opacification. The graph shows the mean±standard deviation of each test group (n=5), and through t-test, *P<0.05 vs alkaline burn group value was considered to be significant.

FIG. 5A is a photograph of a tissue section (Scale bar=1 mm) taken by a virtual microscope (NanoZoomer 2.0 RS, Hamamatsu, Japan); and FIG. 5B is a graph showing the corneal thickness.

FIG. 9 shows the results confirming the inhibitory effect on angiogenesis in HUVEC cells treated with collagen, GDRGD (CPI) and hydroxy proline-GQDGLAGPK (CPII).

FIG. 12 shows the results confirming the effect of inhibiting the choroidal neovascularization by laser irradiation into an animal model followed by treating the same with Avastin or hydroxy proline-GQDGLAGPK (CPII) at a concentration of 5 respectively.

FIG. 16A shows the ocular image results of each group treated with normal saline, Hyp-GQDGLAGPK, collagen, CsA, DQS and HA for 3, 5, 7 and 10 days in NOD.B10.H2b mice (DS) in which the dry stress is removed (Scale bar=1 mm); and FIG. 16B shows changes in the smoothness scores of the corneal surface of mice treated with normal saline, Hyp-GQDGLAGPK, collagen, CsA, DQS and HA as quantitative results of mean±standard deviation. *P<0.05 vs. DS 10D group, #P<0.05 vs. normal saline group, §P<0.05 vs. Hyp-GQDGLAGPK treatment group, ¶P<0.05 vs. CsA treatment group, &P<0.05 vs. CsA treatment group.

FIG. 17A shows the results of hematoxylin and eosin staining (Scale bar=100) confirming the degree of corneal epithelial cell detachment in 10 days after administering normal saline, Hyp-GQDGLAGPK, collagen, CsA, DQS and HA into the corneas of NOD.B10.H2b mice (Scale bar=100 µm); and FIG. 17B is a quantitative result showing the degree of corneal epithelial cell detachment as the mean±standard deviation (* P<0.05 vs. DS 10D group).

FIG. 18A shows the result of PAS staining of the conjunctiva of NOD.B10.H2b mice to which normal saline, Hyp-GQDGLAGPK, collagen, CsA, DQS and HA were administered (Scale bar=200 µm); and FIG. 18B is a quantitative result showing the degree of distribution of conjunctival goblet cells as mean±standard deviation (* P<0.05 vs. DS 10D group).

DETAILED DESCRIPTION

The present invention provides a peptide having an amino acid sequence represented by SEQ ID NO: 1.

A first amino acid of the peptide may be hydroxy proline (Hyd) and more preferably hydroxy proline GQDGLAGPK.

The peptide may be derived from collagen type II α1 and the collagen type II α1 may be isolated from an animal chondrocyte-derived extracellular matrix.

The chondrocyte-derived extracellular matrix may be isolated from cartilage tissue and/or chondrocyte-derived extracellular matrix formed by being secreted from chondrocytes derived from cartilage of an animal, and the animal may be selected from the group consisting of pigs, horses, cows, sheep, goats and monkeys, but it is not limited thereto.

The "peptide" of the present invention is a compound in which at least two α-amino acids are linked by a peptide bond, and is referred to as a dipeptide, a tripeptide, or a tetrapeptide, according to the number of constituent amino acids and an oligopeptide has about 10 or fewer peptide bonds and a polypeptide has a plurality of peptide bonds.

The present invention peptides are prepared using chemical methods (Peptide Chemistry, A practical Textbook. Mikos Bodansky, Springer-Verlag, Berlin). For example, peptides are synthesized by solid state techniques (Roberge J Y et al (1995) Science 269: 202-204), cleaved from resin and purified by high performance liquid chromatography (e.g., Creighton (1983) Proteins Structures and Molecular Principles, WH Freeman and Co., New York N.Y.).

Also, the present invention provides a pharmaceutical composition for preventing or treating an ocular surface disease comprising a peptide having an amino acid sequence represented by SEQ ID NO: 1, as an active ingredient.

The ocular surface disease may be any one selected from the group consisting of corneal opacity, corneal neovascularization, corneal inflammation and corneal fibrosis.

Figure 4:
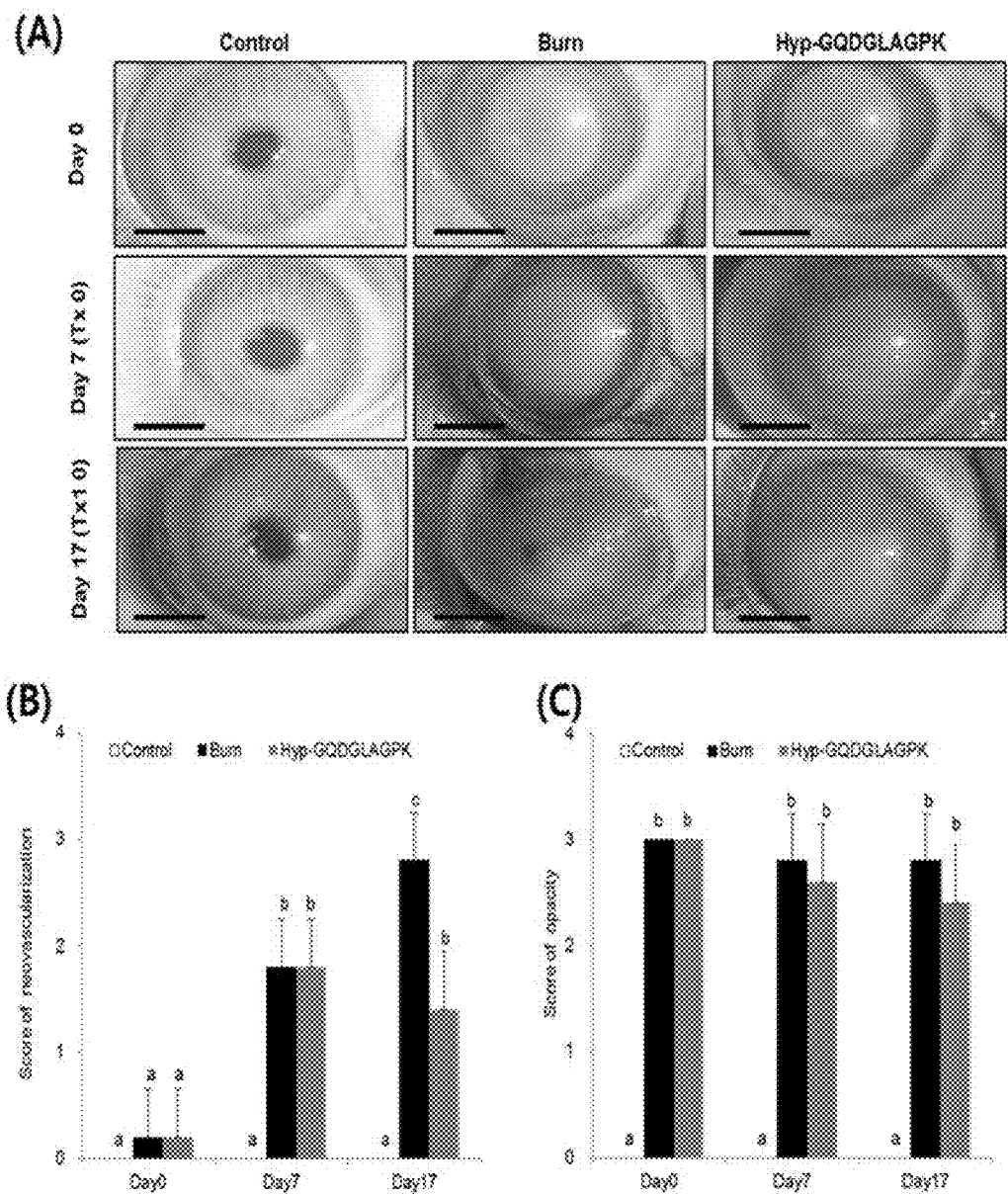
FIG. 4 shows the results confirming the effect of Hyp-GQDGLAGPK in the rabbit cornea burned with alkali.

According to one examples of the present invention, the animal model in which the alkaline burn was induced showed corneal opacity immediately after alkaline burn as shown in FIG. 4A, and corneal neovascularization and opacity were increased after 7 days of alkaline burn, but an animal model in which corneal angiogenesis and opacity were confirmed was treated with normal saline or Hyp- GQDGLAGPK peptide for 10 days (after 17 days of alkaline burn), respectively and the corneal opacity score of the control group significantly increased to 3.0±0.0 as shown in FIG. 4B and FIG. 4C, and the decrease in opacification was observed in the experimental group treated with peptide, as shown in FIG. 4B.

Figure 6:
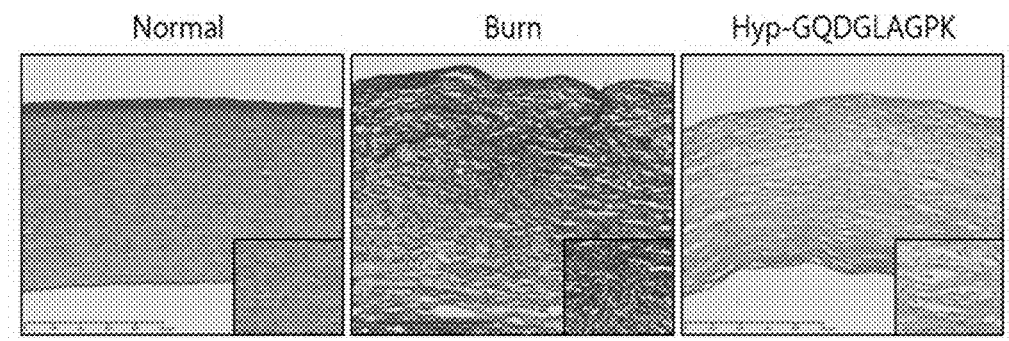
FIG. 6 shows the photographs taken by a virtual microscope (NanoZoomer 2.0 RS, Hamamatsu, Japan) after immunostaining ocular fibroblasts by Masson's trichrome staining method so as to confirm the effect of Hyp-GQDG-LAGPK on changes in fibrosis in rabbit cornea burned with alkali (Scale bar=100 μm) and the portion shown in brown is fibroblast.

According to another example of the present invention, Masson's trichrome staining was performed to confirm the effect of Hyp-GQDGLAGPK peptides on the corneal fibrosis induced by alkaline burn and as shown in FIG. 6, in the case of the control group of alkaline burn, it was confirmed that brown fibroblast formation was increased in the stroma region by the alkaline burn, but the increase of fibroblast was inhibited in the experimental group treated with Hyp-GQDGLAGPK peptide. In addition, H & E staining was performed to confirm the histological change of the cornea according to the alkaline burn and as a result, referring to the upper part of FIG. 7, it was confirmed that the alkaline burn induced epithelial proliferation, inflammatory cell invasion, seizure edema and neovascularization in the cornea.

Figure 5:
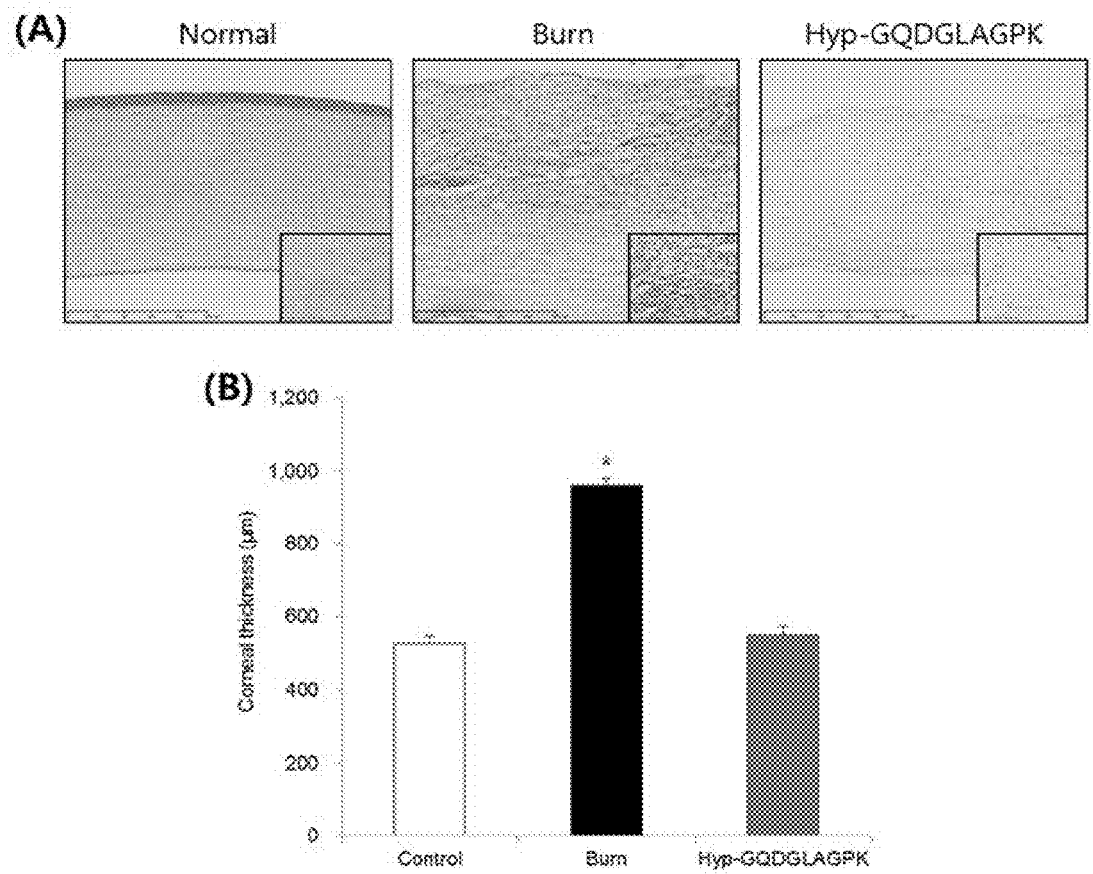
FIG. 5 shows the results confirming the effect of Hyp-GQDGLAGPK on the thickness change of the rabbit cornea burned with alkali.

However, with regard to the histological changes, the experimental group treated with Hyp-GQDGLAGPK peptide showed an advanced improvement effect and as shown in FIG. 5A, the H & E staining results showed that the neovascularization was significantly improved in the peptide-treated tissues.

Figure 8:
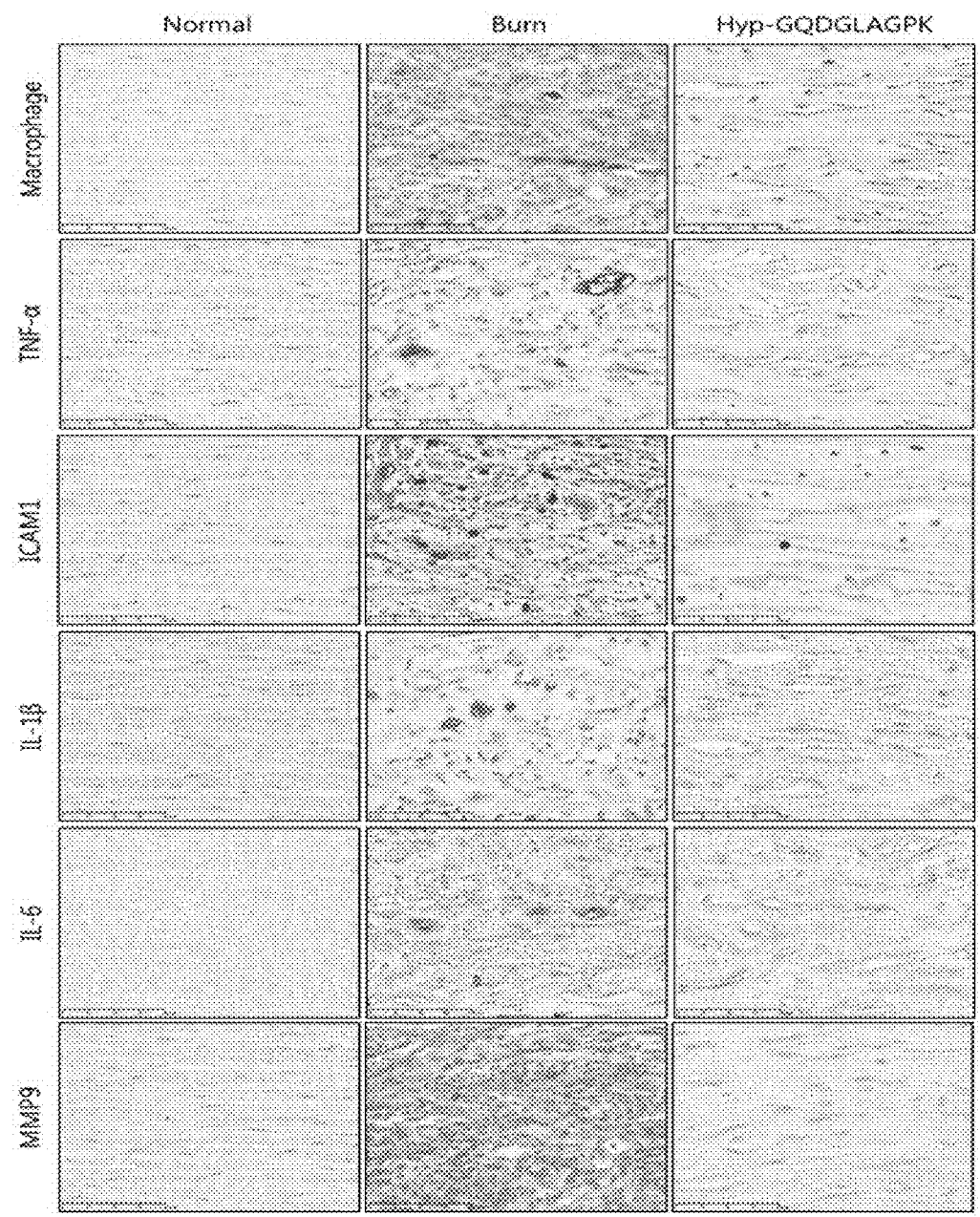
FIG. 8 shows the results confirming the effect of Hyp-GQDGLAGPK on inflammation markers in rabbit burned with alkali and is photographs taken by a virtual microscope (NanoZoomer 2.0 RS, Hamamatsu, Japan) after immunohistochemical staining the tissue sections with specific antibodies such as macrophages, TNFα, ICAM-1, IL-1β, IL-6 and MMP-9 (Scale bar=300 µm).

According to another example of the present invention, in order to confirm the effect of each peptide on the expression of inflammatory markers, corneal sections were immunohistochemical stained for inflammation-specific markers such as macrophages, TNFα, ICAM-1, IL-1β, IL-6 and MMP-9 and as a results, the alkali burn increased macrophage expression in the epithelium and subcutaneous and proliferative matrix as shown in FIG. 8, whereas the experimental group treated with Hyp-GQDGLAGPK peptide effectively inhibited the expression of macrophages. In addition, the expression of inflammatory cytokines including TNFα, IL-1β and IL-6 and ICAM-1 adhesion molecules was observed in the alkaline burn group, but the expression of the inflammatory factors was decreased in the peptide-treated experimental group. Furthermore, the expression of MMP-9 was strongly observed in the cornea of the alkaline burn group, while the expression of MMP-9 was inhibited in the peptide-treated experimental group.

From these results, it was confirmed that Hyp-GQDG-LAGPK peptide is effective in preventing or treating corneal opacity, corneal angiogenesis, corneal inflammation and corneal fibrosis.

The peptide having the amino acid sequence represented by SEQ ID NO: 1 may be derived from collagen type II α1 isolated from a chondrocyte-derived extracellular matrix (CDEM).

More specifically, the chondrocyte-derived extracellular matrix may be isolated from cartilage tissue and/or chondrocyte-derived extracellular matrix formed by being secreted from chondrocytes derived from cartilage of an animal, and the animal may be selected from the group consisting of pigs, horses, cows, sheep, goats and monkeys, but it is not limited thereto.

The peptide having the amino acid sequence represented by SEQ ID NO: 1 may be a peptide of which the first amino acid is hydroxy proline, more preferably a hydroxy proline (Hyp)-GQDGLAGPK.

The peptide having the amino acid sequence represented by SEQ ID NO: 1 may be contained in an amount of 0.1 to 50 parts by weight based on 100 parts by weight of the total pharmaceutical composition.

The pharmaceutical composition may be any one formulation selected from the group consisting of eye drops, injections, granules, tablets, pills, capsules, gels, syrups, suspensions, emulsions, drops and liquids.

The present invention may provide a health food for preventing or improving an ocular surface disease comprising a peptide having an amino acid sequence represented by SEQ ID NO: 1, as an active ingredient.

In addition, the present invention may provide a pharmaceutical composition for preventing or treating macular degeneration comprising a peptide having an amino acid sequence represented by SEQ ID NO: 1, as an active ingredient.

The peptide may be derived from collagen type II α1.

The peptide having the amino acid sequence represented by SEQ ID NO: 1 may be a peptide in which the first amino acid is hydroxy proline, and more preferably proline-GQDGLAGPK.

The peptide may prevent or treat macular degeneration by inhibiting neovascularization of the eye, and the macular degeneration may be age-related macular degeneration, but it is not limited thereto.

According to one example of the present invention, mice were irradiated with a laser to damage the eyeballs, and after 14 days, eyeballs were extracted for H&E staining.

Figure 10:
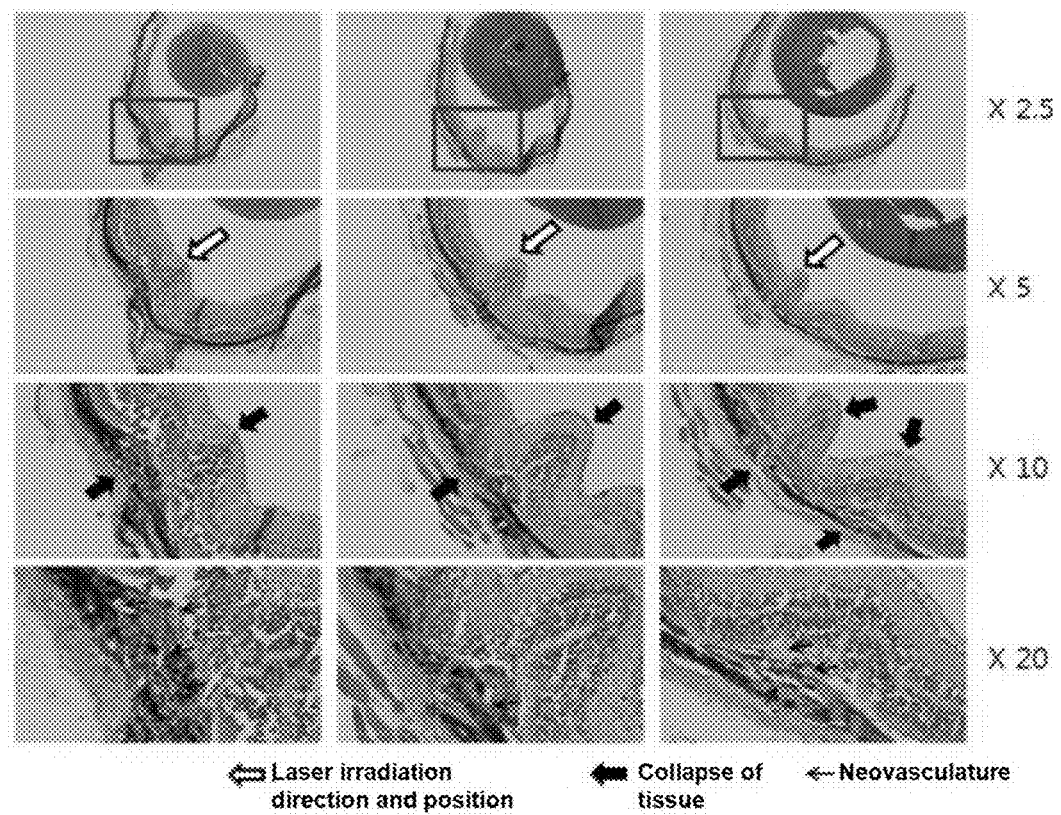
FIG. 10 shows the results confirming the degree of tissue collapse and angiogenesis according to laser irradiation in 14 days after laser irradiation.

As a result, as shown in FIG. 10, it was confirmed that the tissue at the laser irradiation site collapsed and angiogenesis was formed. On the other hand, as shown in FIG. 11, CNV lesions were decreased in the experimental group which is treated with 2 µg of collagen, CPI and CPII after laser irradiation, respectively.

Figure 11:
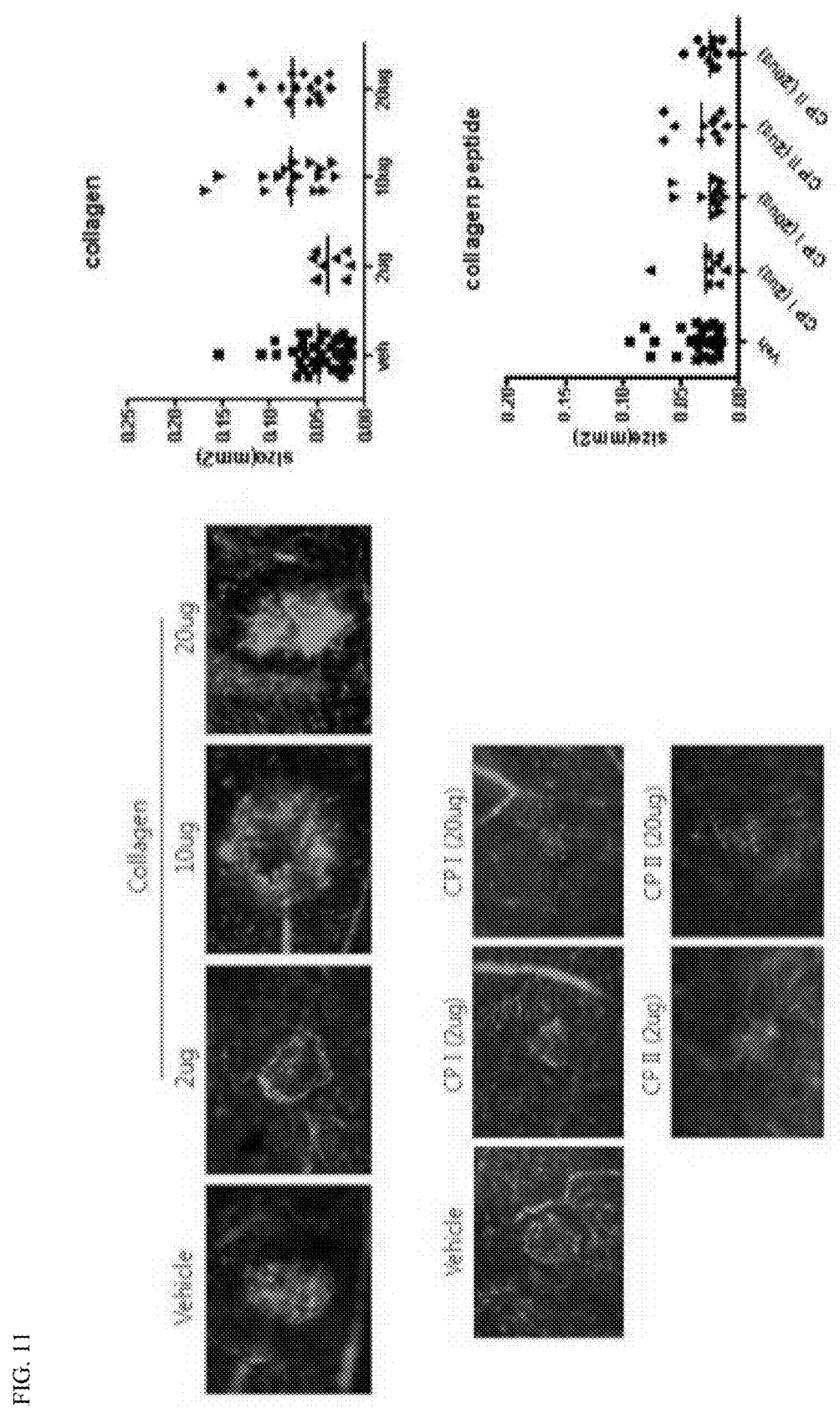
FIG. 11 shows the effect of inhibiting the choroidal neovascularization by laser irradiation into an animal model followed by treating the same with collagen at concentrations of 2, 10 and 20 µg or GDRGD (CPI) and hydroxy proline-GQDGLAGPK (CPII) at concentrations of 2 to 20 µg.

In addition, the choroidal neovascular inhibitory effect of hydroxy proline-GQDGLAGPK (CPII), which has the best anti-angiogenic ability in in vitro tube formation experiments, was compared with that of Avastin, a positive control group, and as shown in FIG. 11, the lesion size was significantly decreased than that of the control group and it was confirmed that it was similar to that of positive control group which was treated with Avastin at same concentration.

From the above results, the hydroxy proline-GQDG-LAGPK peptide can exhibit an excellent therapeutic effect on age-related macular degeneration which is caused by angiogenesis.

The peptide having the amino acid sequence represented by SEQ ID NO: 1 may be contained in an amount of 0.1 to 50 parts by weight based on 100 parts by weight of the total pharmaceutical composition.

The pharmaceutical composition may be any one formulation selected from the group consisting of eye drops, injections, granules, tablets, pills, capsules, gels, syrups, suspensions, emulsions, drops and liquids.

The present invention may provide a health food for preventing or improving macular degeneration comprising a peptide having an amino acid sequence represented by SEQ ID NO: 1, as an active ingredient.

Also, the present invention provides a pharmaceutical composition for preventing or treating dry eye comprising a peptide having an amino acid sequence represented by SEQ ID NO: 1, as an active ingredient.

The peptide having the amino acid sequence represented by SEQ ID NO: 1 may be derived from collagen type II α1.

More specifically, the peptide may be peptide isolated from a chondrocyte-derived extracellular matrix (CDEM), the chondrocyte-derived extracellular matrix may be isolated from cartilage tissue and/or chondrocyte-derived extracellular matrix formed by being secreted from chondrocytes derived from cartilage of an animal, and the animal may be selected from the group consisting of pigs, horses, cows, sheep, goats and monkeys, but it is not limited thereto.

The peptide may be a peptide in which the first amino acid is hydroxy proline, and more preferably, hydroxy proline (Hyp)-GQDGLAGPK.

The peptides can recovers tear production decrease and corneal surface imbalance due to dry stress, and inhibit the detachment of the corneal epithelial cell and the production of inflammatory factor.

Figure 15:
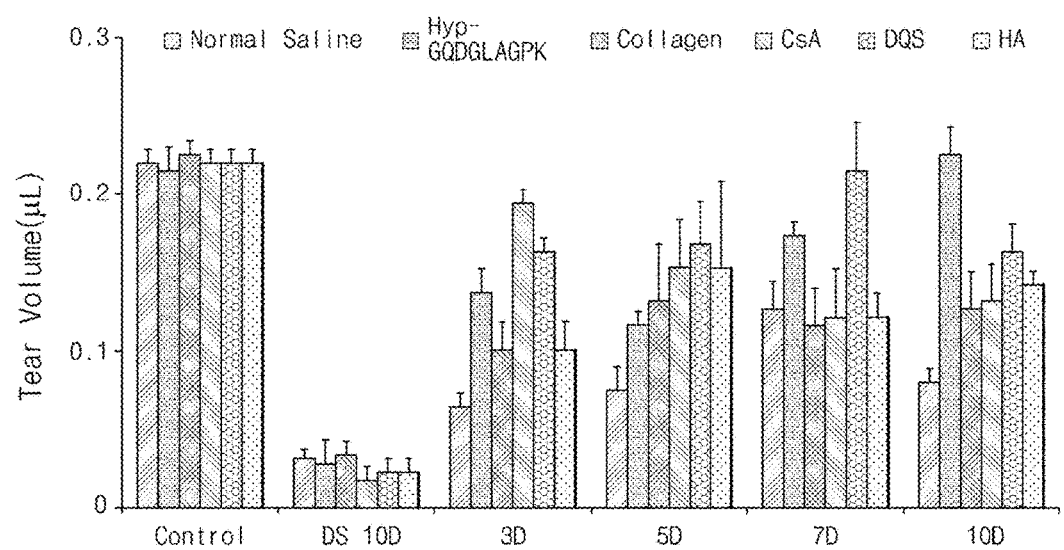
FIG. 15 shows changes in the amount of teardrop in each mouse according to treatment with normal saline, Hyp-GQDGLAGPK, collagen, CsA, DQS and HA in NOD.B10.H2b mice in which the dry stress is removed as quantitative results expressed in means±standard deviation by injecting normal saline, Hyp-GQDGLAGPK, collagen, CsA, DQS and HA into eyes of NOD.B10.H2b mice for 3, 5, 7, and 10 days and measuring the amount of teardrop of the mice. *P<0.05 vs. DS 10D group. #P<0.05 vs. normal saline group. §P<0.05 vs. Hyp-GQDGLAGPK treatment group. ¶P<0.05 vs. CsA treatment group. †P<0.05 vs. DQS treatment group. &P<0.05 vs. CsA treatment group.

According to one example of the present invention, as shown in FIG. 15, the amount of tears in mice exposed to the dry stress was about 85.5% (DS 10D group, 0.03±0.01 µL, p<0.05) lower than that of the normal group (0.22±0.01 µL), but after removal of the dry stress, the amount of tears is increased 7.9 times (p<0.05) after 10 days of treatment in Hyp-GQDGLAGPK treated mice (0.23±0.02 µL), which is confirmed to be about 2.8 times (p<0.05) higher than that of the negative control group, normal saline treatment group (0.08±0.01 µL) and about 1.7 times (p<0.05) higher than that of the positive control group, collagen treatment group (0.13±0.02 µL).

In addition, the tear volume of the Hyp-GQDGLAGPK treatment group was 1.7 times (p<0.05) 1.4 times (p<0.05) and 1.6 times (p<0.05) higher than those of the CsA, DQS and HA treatment groups (0.13±0.02 µL; 0.16±0.02 µL; 0.14±0.01 µL), respectively and thus it was confirmed that the effect of Hyp-GQDGLAGPK on the improvement of tear volume was more effective than the dry eye treatment medicine currently available on the market.

The peptide may be comprised in an amount of 0.1 to 50 parts by weight based on 100 parts by weight of the total pharmaceutical composition.

The pharmaceutical composition may be any one formulation selected from the group consisting of eye drops, injections, granules, tablets, pills, capsules, gels, syrups, suspensions, emulsions, drops and liquids.

The present invention can provide a health food for preventing or improving dry eye comprising a peptide having an amino acid sequence represented by SEQ ID NO: 1, as an active ingredient.

In another embodiment of the present invention, the pharmaceutical composition for preventing or treating an ocular surface disease comprising the peptide as an active ingredient may further comprise at least one additive selected from the group consisting of carrier, excipient, disintegrant, sweetener, coating agent, swelling agent, lubricants, slip modifiers, flavors, antioxidants, buffers, bacteriostats, diluents, dispersants, surfactants, binders and lubricants, which are suitable for conventional use in the manufacture of pharmaceutical compositions.

Specific examples of carriers, excipients and diluents include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil, and solid formulations for oral administration may include tablets, pills, powders, granules, capsules, etc., and these solid preparations can be prepared by mixing with at least one excipient such as starch, calcium carbonate, sucrose or lactose, gelatin, etc. in the composition. Also, in addition to simple excipients, lubricants such as magnesium stearate and talc may be used. Examples of the liquid formulation for oral administration include suspensions, solutions, emulsions, syrups, etc. and various excipients such as wetting agents, sweeteners, fragrances, preservatives, etc. in addition to water and liquid paraffin, which are commonly used as simple diluents. Formulations for parenteral administration include sterilized aqueous solutions, non-aqueous solutions, suspensions, emulsions, freeze-dried formulations, suppositories, and the like. Examples of the non-aqueous solutions or the suspending agent include propylene glycol, polyethylene glycol, vegetable oil such as olive oil, injectable ester such as ethyl oleate, etc. As the suppository base, witepsol, macrogol, tween 61, cacao paper, laurin, glycerogelatin, etc. can be used.

According to one embodiment of the present invention, the pharmaceutical composition can be administered via intravenous, intraarterial, intraperitoneal, intramuscular, intraarterial, intraperitoneal, intrasternal, percutaneous, intranasal, inhalation, topical, rectal, oral, intraocular, or intradermal routes to a subject in a conventional manner.

The preferred dosage of the peptide varies according to the condition and body weight of the subject, the type and degree of the disease, the drug form, the administration route and the period, and can be appropriately selected by those skilled in the art. According to one embodiment of the present invention, the daily dose may be 0.01 to 200 mg/kg, specifically 0.1 to 200 mg/kg, more particularly 0.1 to 100 mg/kg, though it is not limited thereto. The administration can be administered once a day or divided into several doses, by which the scope of the present invention was not limited.

In the present invention, the "subject" may be a mammal including a human, but it is not limited to these examples.

In addition, in the present invention, the health food is used together with other food or food additives other than the peptide of the present invention, and can be suitably used according to a conventional method. The amount to be mixed of the active ingredient can be appropriately determined according to its use purpose, for example, prevention, health or therapeutic treatment.

The effective dose of the compound contained in the health food may be used in accordance with the effective dose of the therapeutic agent, but may be up to the above range for long-term intake for the purpose of health and hygiene or health control purposes, and it is clear that the component can be used in an amount of at least the above range since there is no problem in terms of safety.

There is no particular limitation on the kind of the health food and examples thereof include meat, sausage, bread, chocolate, candy, snack, confectionery, pizza, ramen, other noodles, gums, dairy products including ice cream, various soups, beverages, tea, drinks, alcoholic beverages and vitamin complexes, etc.

Hereinafter, the present invention will be described in detail with reference to the following examples. It should be noted, however, that the following examples are illustrative of the present invention and are not intended to limit the scope of the present invention. The examples of the present invention are provided to more fully describe the present invention to those skilled in the art.

Experimental Example 1

Manufacture of Animal Model of Ocular Surface Disease

An animal experiment for eye and vision studies was conducted according to the Animal Experiment Manual approved by Inje University Medical School and the ARVO Statement (No.; 2014-028).

Twenty-six New Zealand white rabbits of 2.0 to 2.5 kg were purchased from Samtako (Osan, Korea), and a mixture of ketamine hydrochloride (30 mg/kg body weight, Huons, Jecheon, Korea) and xylazine hydrochloride (2.5 mg/kg, Bayer Korea Ltd., Seoul, Korea) was injected into the muscles for general anesthesia and local anesthesia was performed using Alcaine propracaine eye drops (Alcon Inc., Seoul, Korea).

Thereafter, 8 mm filter paper soaked with 1 N NaOH was exposed to the center of the right cornea of the rabbit for 1 minute to prepare an alkaline burn model, and the corneal angiogenesis and corneal opacity were confirmed by the alkaline burn after 7 days of burn.

The rabbits were randomly divided into an alkaline burn group (n=5) and a peptide treated group (n=5). In the alkaline burn group, normal saline was administered 4 times daily and in the peptide-treated group, Hyp-GQDGLAGPK peptide of 10 mg/mL was administered 4 times daily, and the left eye was used as a control group.

After each treatment material was administered for 10 days, H&E staining, Masson's trichrome staining and immunohistochemistry were performed to confirm fibrosis, angiogenesis, inflammation and corneal structure changes.

Experimental Example 2

Identification of Corneal Neovascularization and Opacification

A clinical evaluation of corneal neovascularization and opacification was performed.

A degree of corneal neovascularization was evaluated from 0 to 3 points: 0 point for no angiogenesis, 1 point for angiogenesis at the periphery of the cornea, 2 points for expansion of the angiogenesis to the edge of the pupil, and 3 points for the expansion of the angiogenesis to the corneal center beyond the pupil edge. The corneal angiogenesis was evaluated as 3 points when it was difficult to evaluate the degree of corneal neovascularization due to considerable opacification and extensive symblepharon.

Also, the degree of corneal opacification was evaluated from 0 to 3: 0 point for a clear cornea where the iris part is clearly visible, 1 point for partial opacity in the iris part, 2 points when the edge of the pupil and the iris part looks weak, and 3 points for complete opacification of the iris part and the pupil part.

Experimental Example 3

Masson's Trichrome Staining

The eyeballs were fixed with 3.5% paraformaldehyde, washed and stored in 70% alcohol until paraffin-embedded tissue sections (6 μm) were obtained. To visualize collagen fibrosis and fibrosis grade, Massons trichrome staining of the sections was performed and images of the sections were taken by a virtual microscope (NanoZoomer 2.0 RS, Hamamatsu, Japan).

Experimental Example 4

Chemical Staining for Histological Analysis

For histological analysis, the eyeballs were fixed with 3.5% paraformaldehyde and then frozen in liquid nitrogen with sticking in an optimal cutting temperature compound (OCT; Tissue-Tek, Sakura Fine Technical Co., Ltd., Tokyo, Japan).

Samples were fixed in 4% formaldehyde for 24 hours, dried and then stuck in paraffin wax. Then, tissue sections having thickness of 8 μm was prepared, hematoxylin/eosin (H&E) staining was performed and the images of the sections were photographed by a virtual microscope (NanoZoomer 2.0 RS, Hamamatsu, Japan).

Experimental Example 5

Immunohistochemical Analysis

Tissue sections were cut into 6 μm thickness and used for immunohistochemical analysis.

First, tissue sections were fixed with 3.5% paraformaldehyde and permeated with 0.1% Triton X-100, inactivated 2% bovine serum albumin (BSA; all from Sigma, St. Louis, Mo.) and incubated overnight at 4° C. with anti-CD31(1:1,000; Abcam Inc., Cambridge, Mass.), anti-bFGF(1:1,000; Bioss Inc., Woburn, Mass.), anti-IL-1β, anti-IL-6(1:1,000; Cloud-Clone Corp., Houston, Tex.), anti-MMP-9, anti-ICMA-1, anti-TNFα, anti-macrophage/mononucleus (1:1,000; Abnova Crop., Taipei, Taiwan) and anti-VEGF-A (Abbiotec, San Diego, Calif.) primary antibody.

Thereafter, the secondary antibody was incubated for 45 minutes in the section and the immunological response was visualized with diaminobenzidine (DAB) chromogen, and the section was contrast-stained with Mayer's hematoxylin (Sigma) for 30 seconds at room temperature.

The dyed sections were photographed by a virtual microscope (NanoZoomer 2.0 RS, Hamamatsu, Japan).

Experimental Example 6

Tubing Assay

The antiangiogenic effect of hydroxy proline-GQDG-LAGPK was confirmed by tubing assay using human vascular endothelial cells (HUVEC).

HUVEC cells were stained with calcein-AM and then dispensed on a Matrigel-coated 48-well plate, treated with collagen, CPI and CPII at concentrations together with 50 ng/ml of recombinant human VEGF, and after 4 hours of incubation at 37° C., tube formation was observed by fluorescence microscopy (Leica) and tube length was analyzed by Image lab software (Bio-Rad Laboratories).

Experimental Example 7> Modeling of Experimental Animals and Choroidal Neovascularization (CNV)

C57BL/6 mice were purchased from Orient Bio and the animal experiments was carried out in accordance with the guidelines approved by the University of Inje (No, 2013-053) and ARVO regarding animal use for eye and vision studies. 6-week-old C57BL/6 mice were treated with diode green laser (532 nm, 150 mW, 0.1 sec, 50 μM, photocoagulator) to damage the retinal optic nerve area. Immediately after laser irradiation, CP1, CPII and positive control group Avastin were dissolved in PBS and administered 5 mg each per a day in the eyeball for 5 days. The above experiment for each experiment group was performed using both eyes of five mice each.

Experimental Example 8

Histological Analysis

To observe the tissue changes by laser, mouse eyes were extracted and fixed with 10% formalin and stuck deeply in OCT mixture.

The 8 μm tissue samples treated with the method described above were stained with hematoxylin and eosin (H&E) and photographed by a virtual microscope (Nano-Zoomer 2.0 RS, Hamamatsu, Japan) and analyzed.

Experimental Example 9

Retina-Choroid Flat-Mount

After 14 days of laser irradiation, retina-choroid flat-mount was performed to confirm the inhibitory effect of CPII on CNV lesion size. The mouse was anesthetized and injected with 25 mg/ml of FITC-dextran in 100 ml of retro-orbital. After 30 minutes, the mouse was euthanized and the eyeball was extracted and fixed with 10% formalin and then, the cornea and lens were removed and flat mounted on the cover glass. The neovasculature stained with FITC-dextran was observed by fluorescence microscopy (Leica) and the lesion size was measured by Image J program.

Experimental Example 10

Quantitative Real-Time RT-PCR Analysis

In order to confirm the inhibitory effect of hydroxy proline-GQDGLAGPK on neovascularization-related gene expression, RNA was extracted using RNeasy Mini kit (Qiagen) in mixture of retina and choroid of extracted mice eyeballs, and cDNA was synthesized by using oligo(dT) primer and reverse transcriptase. PCR products were amplified using the specific primer set (COSMOGENETECH, Korea) shown in Table 1 and SYBR Green PCR 2X PreMix (Enzynomics) and for the PCR conditions, the samples were incubated at 95° C. for 10 minutes, and 40 PCR cycles at 95° C. for 15 seconds, 60° C. for 30 seconds and 72° C. for 15 seconds, were performed. Relative quantification was calculated using 2-(DDCT) method [Livak and Schmittgen, 2001; DDCT=(CT, target-CT, actin) control group (CT, target-CT, actin) control group].

TABLE 1

| Target | Primer sequence (5'→3') | |
|---|---|---|
| | Forward | Backward |
| VEGF | ATGAACTTTCTGCT GTCTTGGGTG (SEQ ID NO: 2) | TCACCGCCTCGGCT TGTCACA (SEQ ID NO: 3) |
| ICAM | TGCGTTTTGGAGCT AGCGGACCA (SEQ ID NO: 4) | CGAGGACCATACAG CACGTGCCAG (SEQ ID NO: 5) |
| MCP-1 | TGGCAAGATGATCC CAATGA (SEQ ID NO: 6) | GCAGCACTGTTCGT CACTTCA (SEQ ID NO: 7) |
| GAPDH | ATGGTGAAGGTCGG TGTGAAC (SEQ ID NO: 8) | GTGCCGTTGAATTT GCCGTGA (SEQ ID NO: 9) |

Experimental Example 11

Western Blot

The mixture of retina and choroid of mouse was dissolved in Pro-PREP buffer (iNtRON) containing protease inhibitory cocktail and phosphatase inhibitory cocktail, and the protein was extracted.

The extracted protein was quantified using BCA assay kit (Pierce) and mixed with SDS gel loading buffer, and denatured by boiling at 100° C. for 5 minutes. The proteins were electrophoresed on SDS-PAGE gels and transferred to a nitrocellulose membrane (Millipore), and then to block nonspecific protein binding, the membranes were incubated in 5% skim milk for 1 hour and treated with VEGF, Flk-1, Flt-1, Angiopoetin-2, and β-actin (Santa Cruz Biotechnology) as primary antibody to perform general immunoblotting. Thereafter, immunoreactive protein was detected by ECL kit (Advansta) and multiple gel DOC system.

Experimental Example 12

Modeling of Experimental Animals and Dry Eye

NOD.B10.H2$^b$ mice were purchased from Jackson Laboratory (Bar Harbor, Me., USA). Animal experiments were carried out in accordance with the guidelines approved by the University of Inje (No.; 2014-029) and ARVO regarding animal use for eye and vision research. NOD.B10.H2$^b$ mice at 12-16 weeks old were exposed to 40-50% ambient humidity and ventilation using a fan for 18 hours a day as dry stress and subcutaneously injected with 0.5 mg/0.2 mL muscarinic receptor blocker. In addition, scopolamine hydrobromide (Sigma-Aldrich, St. Louis, Mo.) was injected alternately to the rat hips four times a day for 10 days at 9 am, 12 μm, 3 μm and 6 μm. The mice treated with the above method were euthanized 10 days later and did not restrict animal behavior and food and water intake during the experimental period.

After 10 days of ocular dry stress, the scopolamine injection was stopped, and switched to a normal humidity and temperature environment and the dry stress was removed, 10 mg/ml Hyp-GQDGLAGPK and collagen were dissolved in normal saline to administer 5 μL each 5 times a day for 10 days, and normal saline and 0.1% HA were administered to the eyeball 5 times a day for 10 days. Three mice were used in each of the six experimental groups using both eyes of the mice and all experiments were repeated.

Experimental Example 13

Check of Tear Amount

Tear production was measured by a method reported using phenol red-impregnated cotton threads (Zone-Quick, Oasis, Glendora, Calif.) (Villareal A L, Farley W, Pflugfelder S C. Effect of topical ophthalmic epinastine and olopatadine on tear volume in mice. Eye Contact Lens. 2006; 32 (6): 272-276.). The amount of tear was measured using a medical tweezer, and the thread was placed in the side of the canthus for 20 seconds, and the thread turned into red by wetting with tears was observed with a microscope (SZX7; Olympus Corp, Tokyo, Japan) to express in millimeters. The measured lachrymal fluid in the millimeter was compared with a standard curve expressed as a cotton thread which was soaked with the expected tear amount of mouse of basic solution (1500 mL of 0.9% salt and 5 mL of 5 N NaOH) for 20 seconds.

Experimental Example 14

Evaluation of Bendability of Corneal Surface

As for the curvature of the corneal surface, a reflected image of the white ring was obtained from an optical fiber ring illumination of a stereoscopic microscope (SZX7; Olympus) after anesthetizing the animal. Corneal smoothness was assessed by grading the irregularity of corneal epithelial cells reflected in the white ring of the digital image. Corneal irregularity severity score was calculated by dividing the reflection ring into quadrants and grading into 5 grades according to degree of irregularity. No irregularity is grade 0, irregularity of ¼ (quarter) is grade 1; irregularity of 2/4 (two-quarters) is grade 2; irregularity of ¾ (three-quarters) is grade 3; entire irregularity is grade 4; and severe irregularity is grade 5 and thus all the rings were confirmed.

Example 1

Protein Analysis and Peptide Synthesis

The protein analysis of animal chondrocyte-derived extracellular matrix was performed in Baek's group of Center of Biomedical Mass Spectrometry (Diatech Korea Co., Ltd., Seoul, Korea).

A hydroxy proline-GQDGLAGPK (Hyp-GQDGLAGPK SEQ ID NO: 1) was obtained by the above protein analysis, which corresponds to a portion of amino acid sequence of collagen type II α1 protein and the peptides were synthesized in BIOCELTRAN (Chuncheon, Korea), as shown in FIG. 1.

Figure 2:
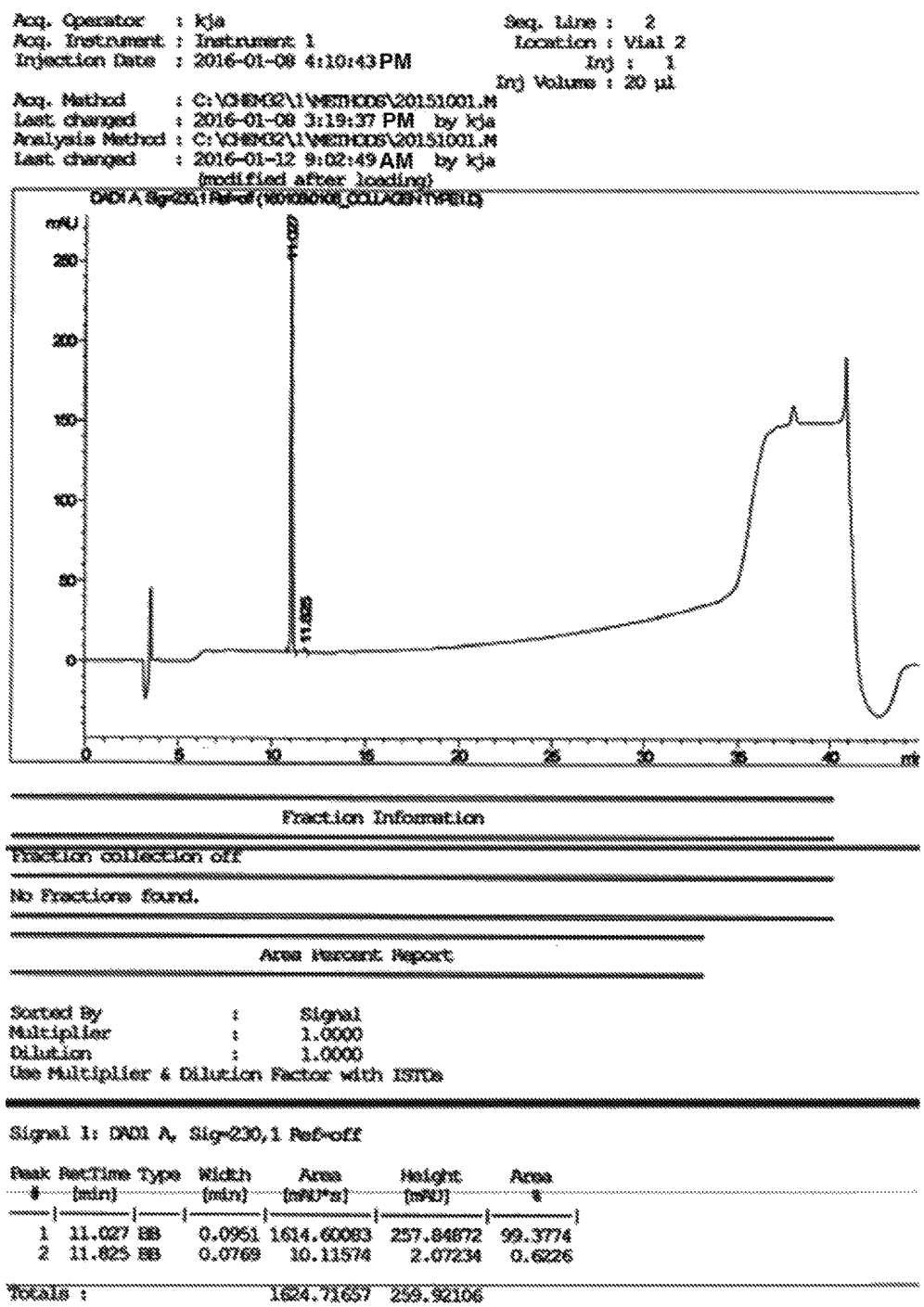
FIG. 2 shows the results analyzing the purity of the hydroxy proline-GQDGLAGPK peptide using HPLC.

HPLC was performed to confirm the purity of the synthesized hydroxyl proline-GQDGLAGPK and as a result, it was confirmed that the hydroxyl proline-GQDGLAGPK peptide was synthesized with a purity of 99.3% as shown in FIG. 2.

Figure 3:
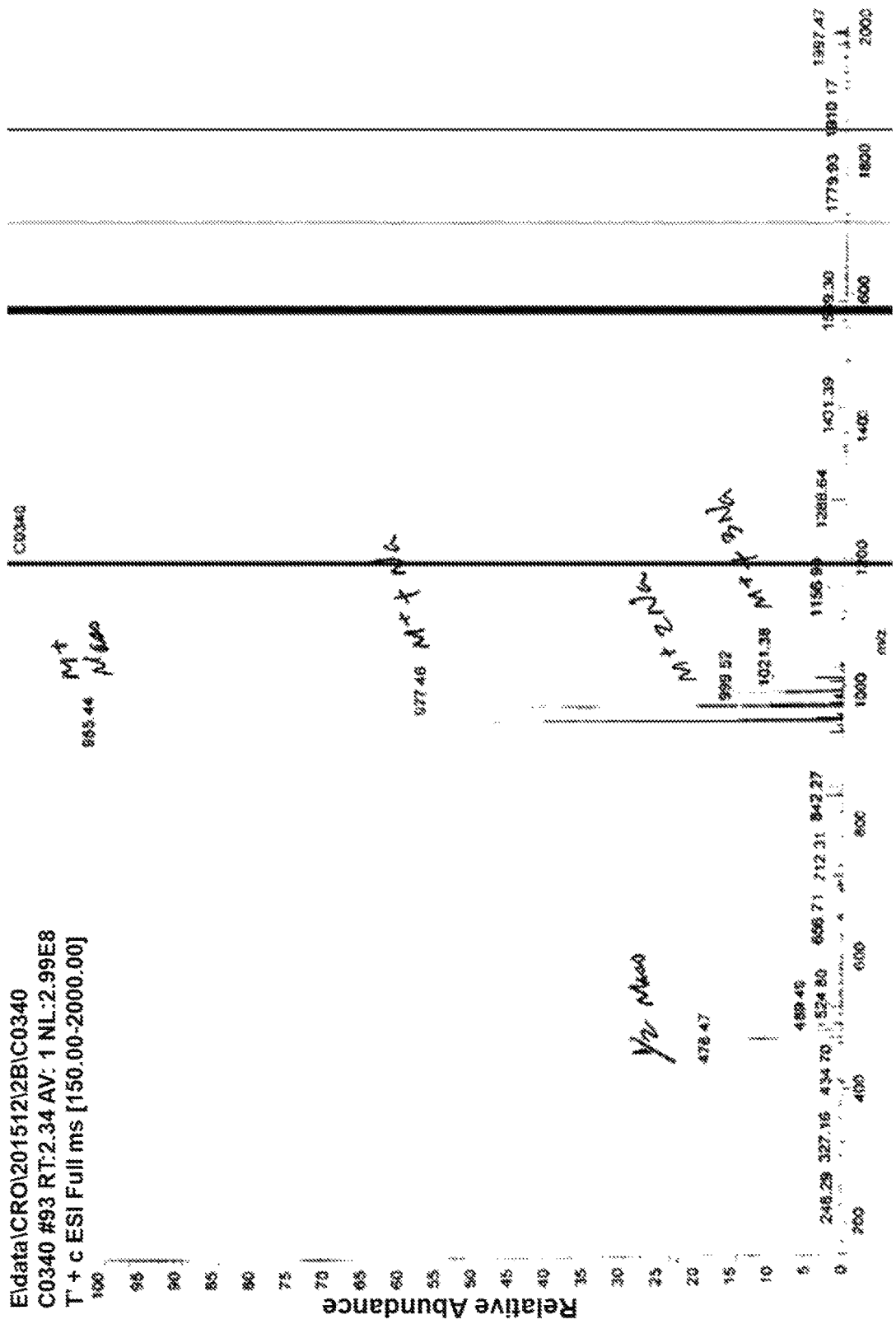
FIG. 3 shows the results confirming the molecular weight of the hydroxy proline-GQDGLAGPK peptide by Ion-Mass.

In addition, as a result of confirming the molecular weight of the hydroxyl proline-GQDGLAGPK peptide through Ion-Mass, it was confirmed that the molecular weight of the hydroxyl proline-GQDGLAGPK peptide was 654.99 as shown in FIG. 3.

Example 2

Identification of Corneal Neovascularization and Opacification Change by Peptide After 7 days of alkaline burn of cornea, clinical evaluation of corneal neovascularization and opacification was performed.

As a result, it was confirmed that corneal opacity was occurred immediately after alkaline burn as shown in FIG. 4A and corneal neovascularization and opacity were increased after 7 days of alkaline burn.

After corneal neovascularization and opacification were confirmed, treatment with normal saline or Hyp-GQDGLAGPK peptide for 10 days (after 17 days of alkaline burn) resulted in a significant increase in the corneal opacity score of the control group to 3.0 as shown in FIG. 4B and FIG. 4C, and the neovascularization score was 2.8, indicating that the neovascularization extended beyond the pupil margin to the corneal center.

On the other hand, as shown in FIG. 4B, it was confirmed that the reduction effect of opacity was shown in the peptide-treated experimental group.

From the above results, it was confirmed that Hyp-GQDGLAGPK peptide is effective inhibiting corneal opacification.

Example 3

Confirmation of Corneal Thickness Change by Peptide

The corneal thickness of H&E stained sections photographed with a virtual microscope (NanoZoomer 2.0 RS, Hamamatsu, Japan) was analyzed using the NDP view program (Hamamatsu, USA).

As a result, it was confirmed that the corneal thickness increased from the normal range of 526.6 µm to 960.6 µm after the alkaline burn, as shown in FIG. 5B.

However, after 10 days of Hyp-G-GQDGLAGPK peptide treatment, it was confirmed that the thickness of the cornea was reduced to 550.0 µm ($p<0.05$) in the peptide-treated experimental group than in the alkaline burn group.

Example 4

Identification of Effect of Inhibiting Corneal Fibrosis of Peptides

Masson's trichrome staining was performed to confirm the effect of Hyp-GQDGLAGPK peptide on the corneal fibrosis induced by alkaline burn.

As a result, the alkaline burn control group was confirmed to increase the brown fibroblast formation in the stroma part by the alkaline burn, as shown in FIG. 6, but it was confirmed that the fibroblast increase was suppressed in the experimental group treated with Hyp-GQDGLAGPK peptide.

From the above results, it was confirmed that Hyp-GQDGLAGPK peptide inhibits the increase of fibroblasts and is effective in inhibiting corneal fibrosis.

Example 5

Identification of Effect of Inhibiting Corneal Neovascularization of Peptides

H&E staining was performed to confirm histological changes of the cornea according to alkaline burn.

Figure 7:
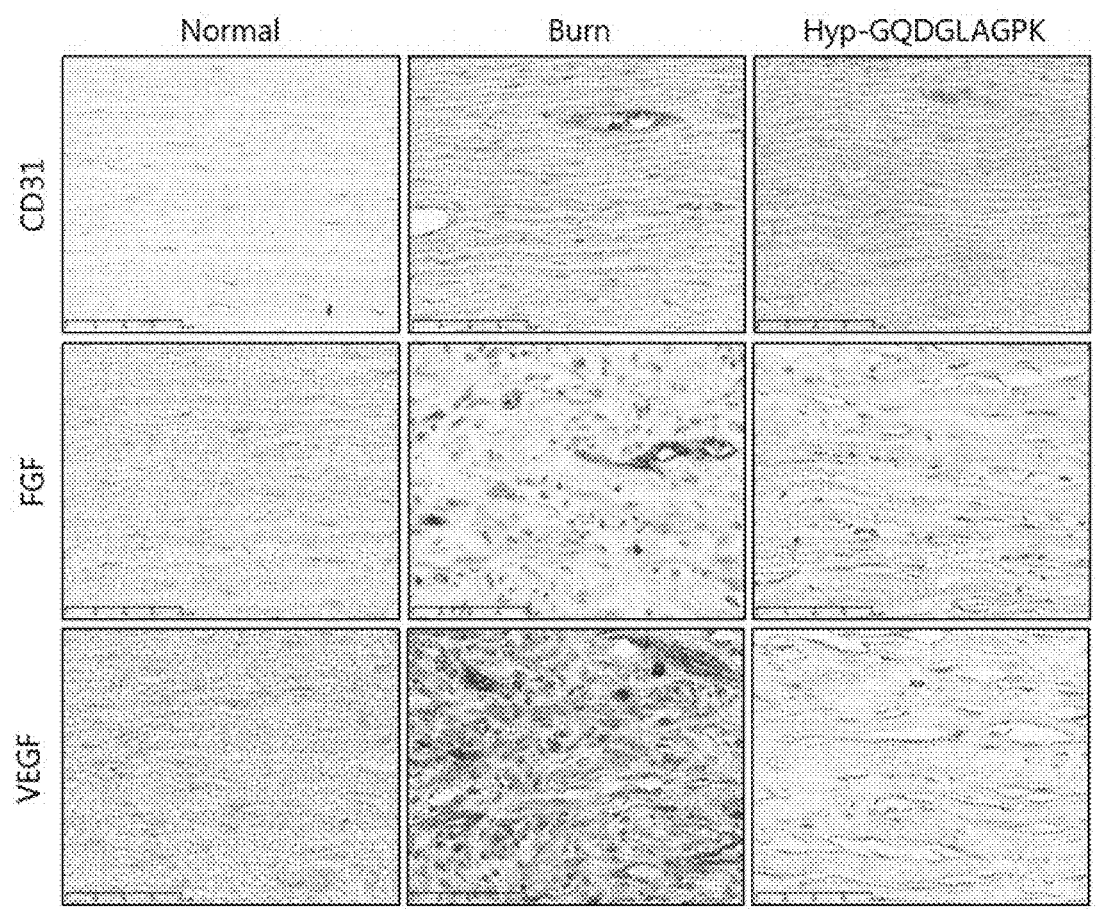
FIG. 7 shows the results confirming the effect of Hyp-GQDGLAGPK on angiogenesis markers in rabbit burned with alkali and is photographs of tissue sections immunostained with specific antibodies, CD31, FGF and VEGF by a virtual microscope (NanoZoomer 2.0 RS, Hamamatsu, Japan) (Scale bar=300 μm).

As a result, referring to the upper part of FIG. 7, it was confirmed that epithelial proliferation, inflammatory cell invasion, seizure edema, and neovascularization were induced in the cornea by the alkaline burn.

However, with regard to the above histological changes, the group treated with Hyp-GQDGLAGPK peptide showed an advanced improvement effect and as shown in FIG. 5A, the H&E staining results also showed that the neovascularization was significantly improved in the peptide-treated tissues.

From the above results, it was confirmed that Hyp-GQDGLAGPK peptide affects neovascularization and thus, the alkaline burned cornea was treated with Hyp-GQDGLAGPK peptides and Immunostaining was performed on the corneal sections using CD31, FGF and VEGF, which are specific markers of corneal neovascularization.

As a result, it was confirmed that CD31, FGF and VEGF neovascularization markers were strongly expressed in fibroblast matrix cells according to the alkaline burn, as shown in FIG. 7.

However, significant decreases of CD31, FGF and VEGF were observed in the epithelium, subepithelium and matrix in the peptide-treated group.

From the above results, it was confirmed that Hyp-GQDGLAGPK peptide is effective in inhibiting corneal neovascularization.

Example 6

Identification of Anti-Inflammatory Effects of Peptides

As a result of the above H&E staining, it was confirmed that the inflammatory cells penetrated into the cornea by the alkaline burn. Therefore, in order to confirm the effect of each peptide on the expression of inflammatory markers, immunostaining was performed with inflammatory specific markers such as macrophages, TNFα, ICAM-1, IL-1β, IL-6 and MMP-9 in the corneal sections.

As a result, it was confirmed that the alkaline burn increased the expression of macrophages in the epithelium, subepithelium and proliferative matrix as shown in FIG. 8, whereas the expression of macrophages was effectively inhibited in the experimental group treated with Hyp-GQDGLAGPK peptide. In addition, the expression of inflammatory cytokines including TNFα, IL-1β and IL-6 and ICAM-1 adhesion molecules was increased in the alkaline burn group, but the expression of the inflammatory factors was decreased in the peptide-treated experimental group. Furthermore, the expression of MMP-9 was strongly observed in the cornea of the alkaline burn group, while the expression of MMP-9 was inhibited in the peptide-treated experimental group.

Example 7

Confirmation of Effect of Inhibiting Neovascularization of Peptides

Tubing assay using human vascular endothelial cells (HUVEC) was performed to confirm the anti-angiogenic effect of hydroxyl proline-GQDGLAGPK.

As a result, as shown in FIG. 9, the tube formation of the VEGF-treated group was increased about at least 1.5 times than that of the VEGF-untreated group, whereas the experimental groups treated with collagen, CPI and CPII showed significant inhibition of angiogenesis. In particular, CPII inhibited the tube formation ifs a concentration-dependent manner and decreased to almost same extent of angiogenesis of the VEGF-untreated group. It was also confirmed to be similar level of group treated with Avastin, a remedy of an age-related macular degeneration.

Example 8

Confirmation of Effect of Inhibiting Choroidal Neovascularization of Peptides

An eyeball of mouse was irradiated by laser in the same manner of Experimental Example 7 and 14 days after the laser irradiation, the eyeball was extracted and H&E staining was performed.

As a result, as shown in FIG. 10, it was confirmed that the tissue at the laser irradiation site collapsed and an angiogenesis was formed. On the other hand, as shown in FIG. 3, CNV lesions were reduced in the experimental group treated with collagen, CPI and CPII by intraocular injection for 5 days, respectively, which was all treated at 2 µg.

In order to compare the effect of inhibiting choroidal neovascularization of hydroxyl proline-GQDGLAGPK (CPII), which has the best anti-angiogenic efficacy in the in vitro tube formation experiment, with the positive control group Avastin, respective 5 µg of CPII and Avastin were injected intraocularly for 5 consecutive days immediately after laser irradiation, eyeballs were extracted 14 days after laser irradiation and blood vessels were stained with FITC-dextran, and flat-mount experiments were performed to measure CNV lesion size.

As a result, as shown in FIG. 11, the lesion size of the CPII-treated group was significantly decreased smaller than that of the control group, and it was confirmed to be similar to the lesion size of the positive control group treated with Avastin at the same concentration.

Example 9

Confirmation of Effect of Inhibiting Neovascularization Related Gene and Protein of Peptides After 14 days of laser irradiation in mouse, RNA was extracted from retina and choroid to analyze the gene expression by real-time RT-PCR.

As a result, as shown in FIG. 12, the expression of VEGF, which is a typical neovascularization related gene, was increased about 55 times in the laser-treated group, but it was decreased to the level similar to that of the laser-untreated group in the Avastin-treated group and CPII-treated group.

On the other hand, the ICAM and MCP-1 genes were increased about 300 times and 10 times in the laser-treated group, respectively, but they were also significantly decreased in the CPII-treated group.

Also, in order to evaluate the effect of CPII on the expression of the neovascularization-related protein markers, proteins were extracted from the retina and choroid after 14 days of the laser irradiation to perform immunoblotting of VEGF, VEGFR-1 (Flt-1), VEGR-2 (Fik-1) and Angiopoietin 2.

Figure 13:
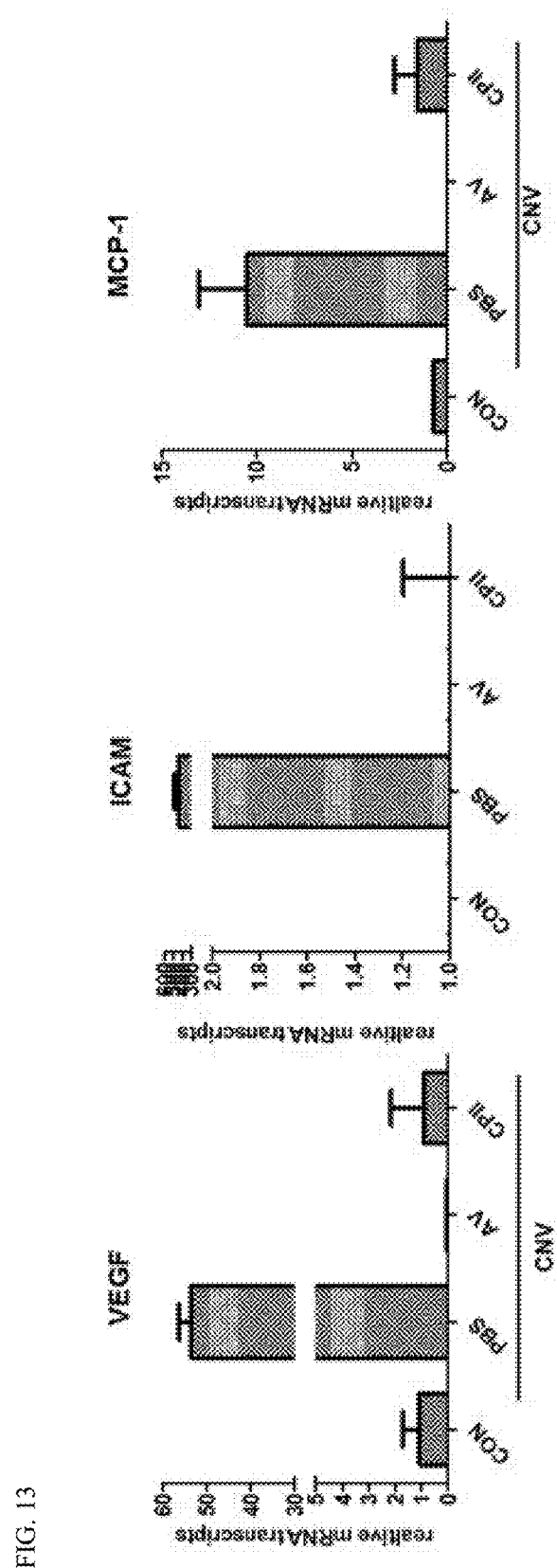
FIG. 13 shows the results of real-time RT-PCR confirming gene expression levels of VEGF, ICAM and MCP-1 by laser irradiation into an animal model followed by treating the same with Avastin or hydroxy proline-GQDGLAGPK (CPII) at a concentration of 5 µg, respectively and extracting RNA from the retina and choroid after 14 days of laser irradiation.
Figure 14:
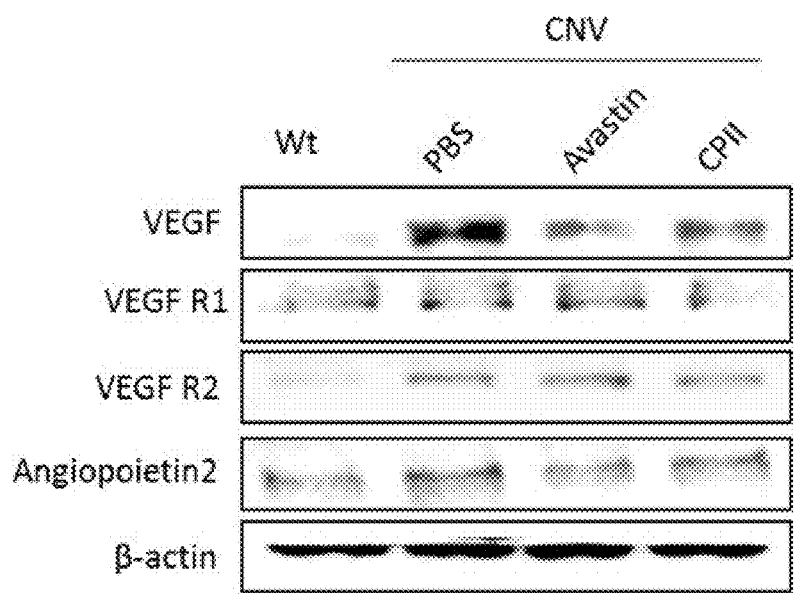
FIG. 14 shows the results of Western blot confirming protein expression levels of VEGF, VEGFR-1(Flt-1), VEGR-2(Flk-1) and Angiopoietin 2 in the obtained retina and choroid extract by laser irradiation into an animal model followed by treating the same with Avastin or hydroxy proline-GQDGLAGPK (CPII) at a concentration of 5 µg, respectively and extracting after 14 days of laser irradiation.

As a result, as shown in FIG. 13, it was confirmed that the expression of Angiopoietin2 and VEGFR-1, -2, which are the angiogenesis promoting factors, was significantly increased by laser irradiation. Especially, the expression of VEFG which is known to play the most important role in neovascularization was markedly increased. However, in the CPII-treated experimental group, the expression of the above proteins was markedly decreased, and it was almost similar to that of Avastin, a remedy of age-related macular degeneration Example 10

Confirmation Tear Generation Effect

The degree of tear generation was measured by phenol red-impregnated cotton threads.

As a result, as shown in FIG. 15, it was confirmed that the amount of tear of NOD.B10.H2$^b$ mice was decreased to a significant level, about 85.5% by the dry stress, comparing with the normal group (0.22±0.01 µL) (DS 10D group, 0.03±0.01 µL, p<0.05). On the other hand, in the group treated with Hyp-GQDGLAGPK (0.23±0.02 µL) after eliminating the dry stress, the tear amount was increased 7.9 times (p<0.05) at 10 days after the treatment and about 2.8 times (P<0.05) of the negative control group treated with normal saline (0.08±0.01 µL) (P<0.05) and about 1.7 times (p<0.05) of the positive control group (0.13±0.02 μL) treated with collagen, respectively.

In addition, compared with CsA (Cyclosporine A; 0.13±0.02 μL), DQS (0.16±0.02 μL) and HA (Hyaluni; 0.14±0.01 μL) which are remedies of dry eye, the tear amount of the group treated with Hyp-GQDGLAGPK were increased by 1.7 times (p<0.05), 1.4 times (p<0.05), and 1.6 times (p<0.05), respectively.

From the above results, it was confirmed that Hyp-GQDGLAGPK recovered the decreased tear amount to a level higher than the commercially available dry eye remedy.

Example 11

Confirmation Bendability of Corneal Surface

The degree of corneal curvature in each experiment group was quantified to confirm the bendability of the corneal surface.

Figure 16:
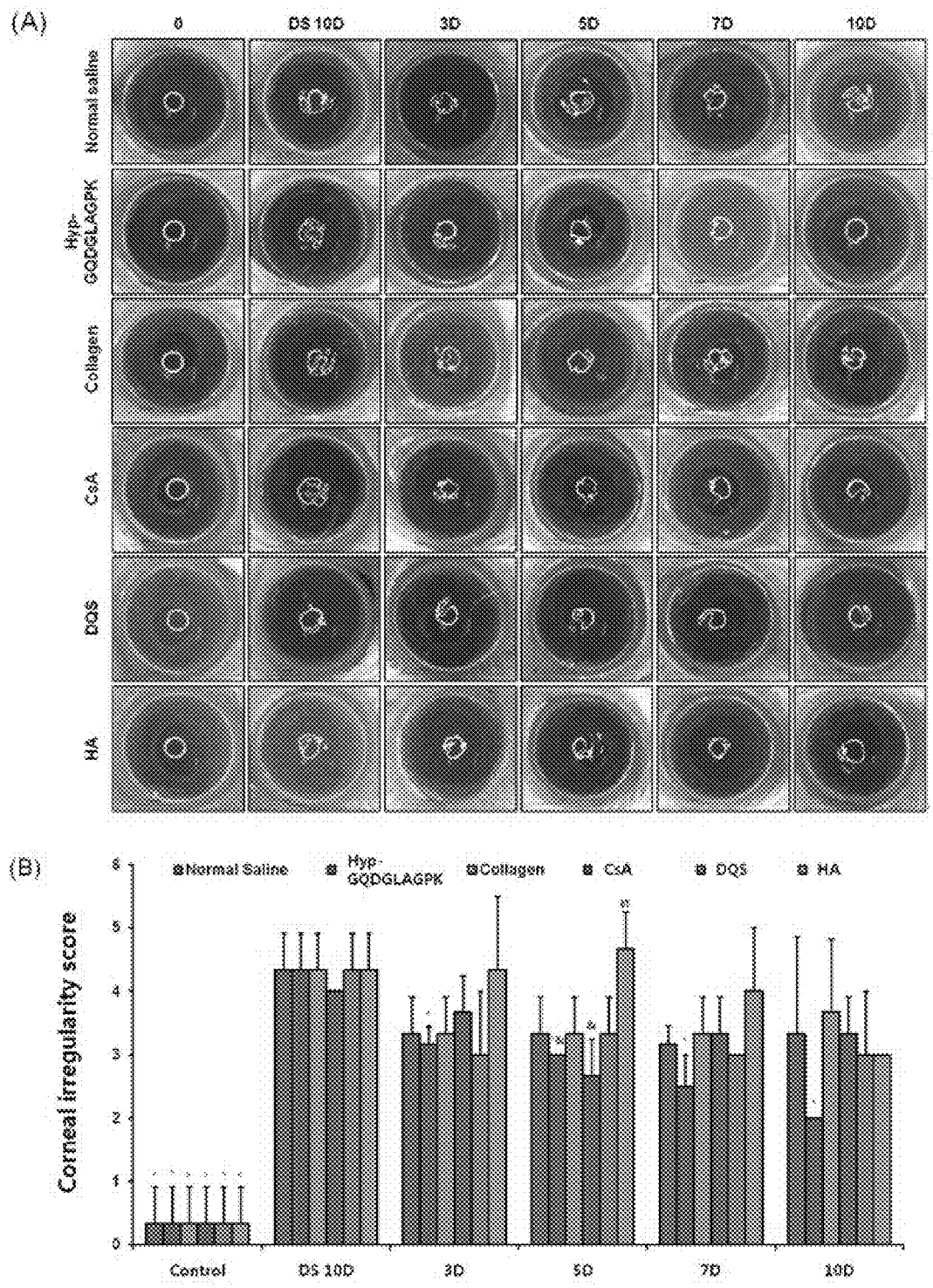
FIG. 16 shows the effect of Hyp-GQDGLAGPK peptide on corneal surface flexion.

As a result, as shown in FIG. 16, it was confirmed that the degree of curvature of the corneal surface of a mouse exposed to the dry stress for 10 days was about 13 times (4.33±0.58 points; p<0.05) higher than that of the normal corneas (0.33±0.58 points). On the other hand, the bendability of the corneal surface in the group treated with Hyp-GQDGLAGPK (2.0±0 points) was significantly decreased by 53.8% (p<0.05) at day 10 after removal of the dry stress, which is decreased by 40% (p<0.05) of the negative control group treated with normal saline (3.33±1.53 points) and 45.5% (p<0.05) of the positive control group treated with collagen (3.67±1.16 points).

In addition, compared with the groups treated with CsA, DQS and HA (3.33±0.58 points; 3.0±1.0 points; 3.0±0 points) which are remedies of dry eye, the degree of curvature of the conical surface was decreased by 40% (p<0.05), 33.3% (p<0.05) and 33.3% (p<0.05), respectively.

From the above results, it was confirmed that Hyp-GQDGLAGPK is more effective in improving the curvature of the corneal surface than dry eye remedy.

Example 12

Confirmation of Effect of Inhibiting Corneal Epithelial Cell Detachment

To confirm the effect of peptides on corneal epithelial cell detachment, corneas of mouse of each experimental group were H&E stained.

Figure 17:
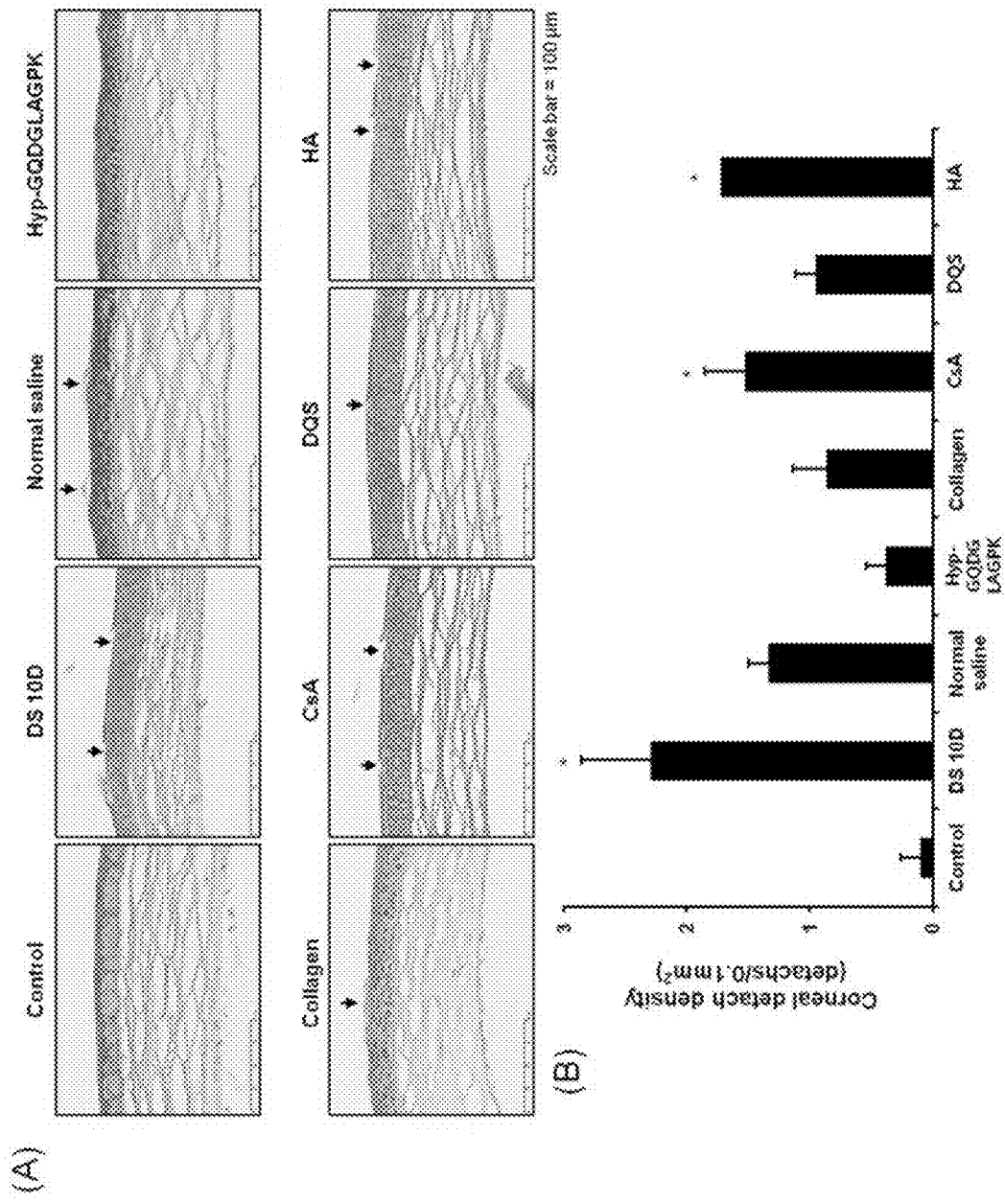
FIG. 17 shows the effect of Hyp-GQDGLAGPK peptide on corneal epithelial cell detachment.

As a result, as shown in FIG. 17, the epithelial cell detachment of the cornea was increased by 24 times (2.29±0.57/0.1 mm$^2$, p<0.05) by dry stress. On the other hand, the corneal epithelial cell detachment was reduced by 83.3% (p<0.05) in Hyp-GQDGLAGPK treated group (0.38±0.17/0.1 mm$^2$) after removal of the dry stress. In addition, the corneal epithelial cell detachment was decreased by 71.4% (p<0.05) of the negative control group treated with normal saline (1.33±0.17/0.1 mm$^2$) and 55.6% (p<0.05) of the positive control group treated with collagen (0.86±0.29/0.1 mm$^2$).

In addition, compared with the groups treated with CsA, DQS and HA which are remedies of dry eye (1.52±0.33/0.1 mm$^2$; 0.095±0.17/0.1 mm$^2$; 1.71±0/0.1 mm$^2$), it was decreased by 75% (p<0.05), 60% (p<0.05) and 77.8% (p<0.05), respectively.

From the above results, it was confirmed that Hyp-GQDGLAGPK is more effective in reducing the corneal epithelial cell detachment than dry eye remedy.

Example 13

Confirmation of Effect on Distribution of Conjunctival Goblet Cells

The distribution of conjunctival goblet cells according to eye drop in dry eye mice was observed.

Figure 18:
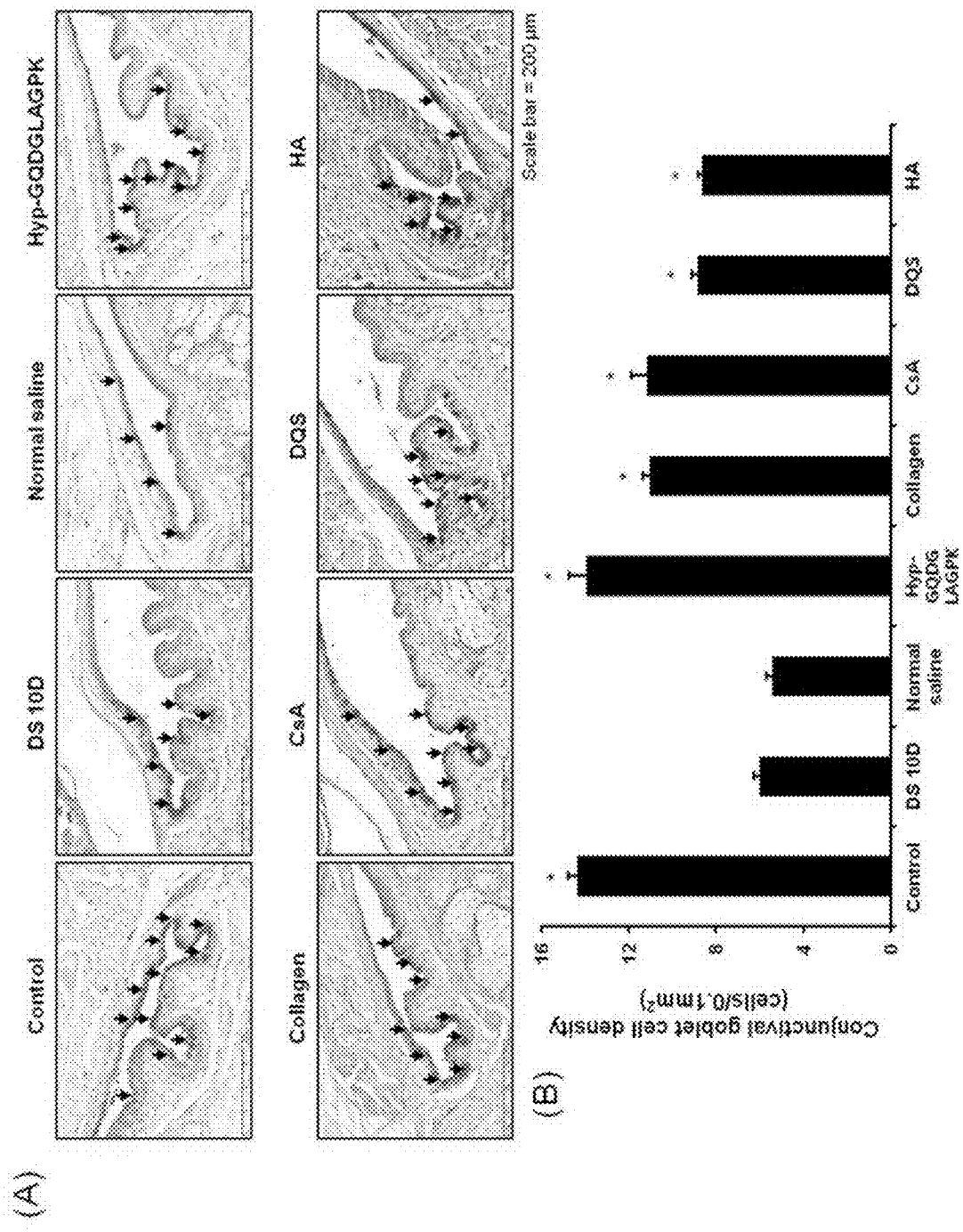
FIG. 18 shows the effect of Hyp-GQDGLAGPK peptide on the distribution of conjunctival goblet cells.

As a result, as shown in FIG. 18, the goblet cell was decreased by 58.2% (6.02±0.29/0.1 mm$^2$, p<0.05) compared to the normal conjunctiva (14.38±0.44/0.1 mm$^2$) by dry stress. On the other hand, the goblet cell was recovered by 2.3 times (p<0.05) in Hyp-GQDGLAGPK treated group (13.9±0.83/0.1 mm$^2$) after removal of the dry stress, which is increased 2.6 times (p<0.05) of the negative control group treated with normal saline (5.43±0.29/0.1 mm$^2$) and 1.3 times (p<0.05) of the positive control group (11.05±0.33/0.1 mm$^2$) treated with collagen, respectively.

In addition, compared with the groups treated with CsA, DQS and HA which are remedies of dry eye (11.14±0.76/0.1 mm$^2$; 8.86±0.29/0.1 mm$^2$; 8.67±0.17/0.1 mm$^2$), it was recovered 1.2 times (p<0.05), 1.5 times (p<0.05) and 1.6 times (p<0.05), respectively.

From the above results, it was confirmed that Hyp-GQDGLAGPK is more effective in reducing the corneal epithelial cell detachment than dry eye remedy.

From the above results, the distribution of goblet cells in the conjunctiva was improved in the remaining treatment groups except for the group treated with normal saline, but it was confirmed that it was significantly increased in the cornea of the animal treated with Hyp-GQDGLAGPK.

Example 14

Confirmation of Anti-Inflammatory Effects in Dry Eye Mouse Model

Immunostaining of TNF-α, ICAM-1, VCAM-1, MMP-2 and MMP-9 was performed in the lacrimal gland to evaluate the effect of Hyp-GQDGLAGPK on the expression of inflammatory response factors in dry eye mouse models.

Figure 19:
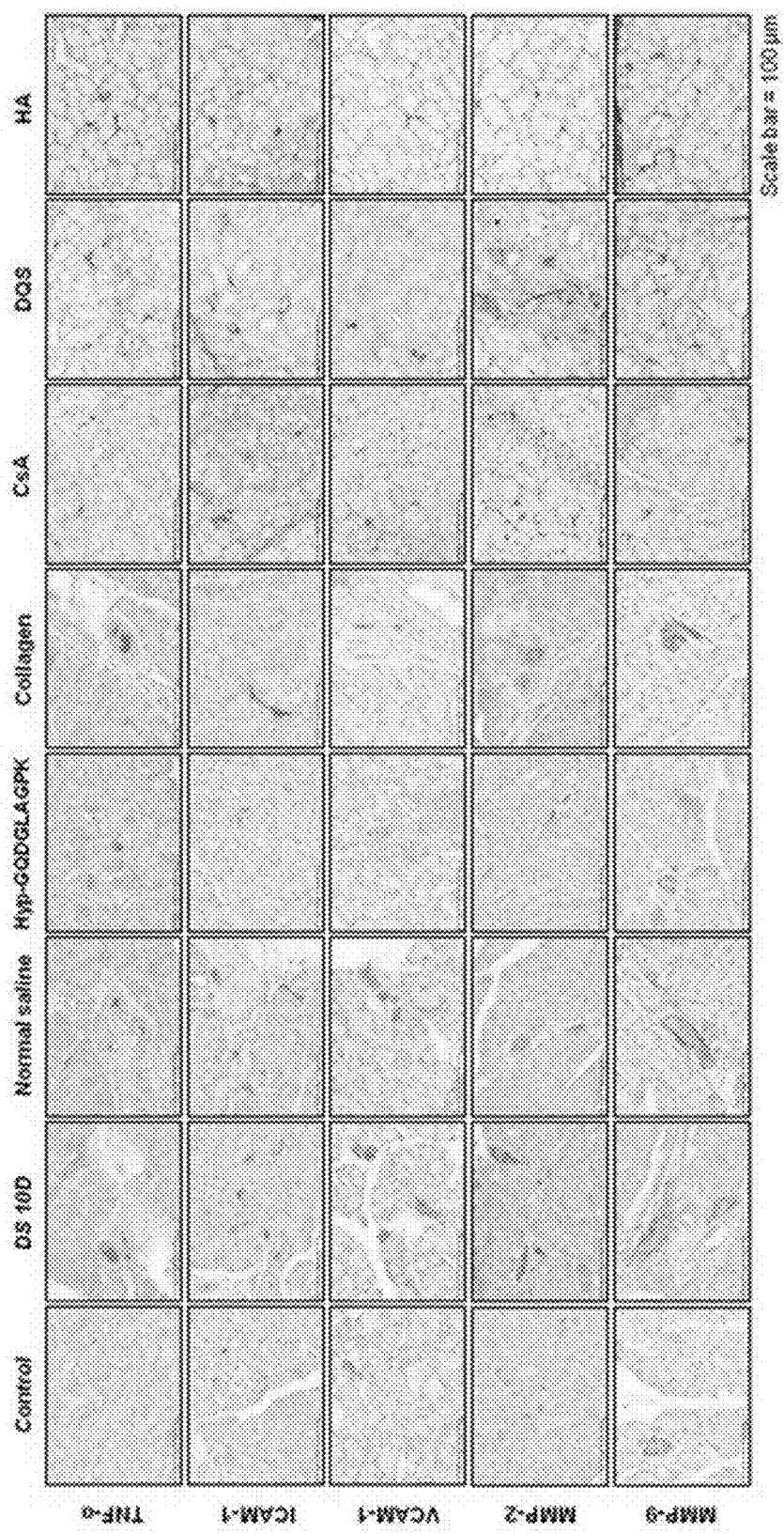
FIG. 19 shows the results of immunohistochemical analysis of TNF-α, ICAM-1, VCAM-1, MMP-2 and MMP-9 expression levels in the lacrimal gland of NOD.B10.H2b mice and the results confirming the degree of expression of the inflammatory factors by administering normal saline, Hyp-GQDGLAGPK, collagen, CsA, DQS and HA into the mice in which the dry stress is removed and passing 10 days (Scale bar=100 µm).

As a result, as shown in FIG. 19, the expression of inflammatory cytokines TNF-α and adhesion molecules ICAM-1 and VCAM-1 was markedly increased in the lacrimal gland by dry stress, MMP-2 and MMP-9 of lacrimal gland were also increased significantly by the dry stress. However, in the lacrimal gland of the Hyp-GQDGLAGPK-treated mouse model, the expression of the inflammation-related factors was markedly reduced, and it was confirmed that it was significantly inhibited compared with the mouse models treated with CsA, DQS and HA which are remedies of dry eye While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method of treating macular degeneration in a subject in need thereof, comprising:
providing a pharmaceutical composition comprising a peptide having an amino acid sequence represented by SEQ ID NO: 1, as an active ingredient; and
administering the pharmaceutical composition to the subject, wherein the macular degeneration is prevented or treated.

2. The method of claim 1, wherein the peptide is derived from collagen type II α1.

3. The method of claim 1, wherein the peptide inhibits ocular neovascularization.

4. The method of claim 1, wherein the peptide having the amino acid sequence represented by SEQ ID NO: 1 is contained in an amount of 0.1 to 50 parts by weight based on 100 parts by weight of total amount of the pharmaceutical composition.

5. The method of claim 1, wherein the pharmaceutical composition is any one formulation selected from the group consisting of eye drops, injections, granules, tablets, pills, capsules, gels, syrups, suspensions, emulsions, drops and liquids.

6. A health food for improving macular degeneration comprising a peptide having an amino acid sequence represented by SEQ ID NO: 1, as an active ingredient.

* * * * *